US009096669B2

(12) United States Patent
Ke et al.

(10) Patent No.: US 9,096,669 B2
(45) Date of Patent: Aug. 4, 2015

(54) HUMANIZED ANTI-TNF-α ANTIBODY AND ANTIGEN-BINDING FRAGMENT (FAB) THEREOF AND USE OF THE SAME

(75) Inventors: Xiao Ke, Sichuan (CN); Xiaoping Gao, Sichuan (CN)

(73) Assignee: CHENGDU KANGHONG BIOTECHNOLOGIES CO., LTD., Sichuan (CN)

( * ) Notice: Subject to any disclaimer, the term of this patent is extended or adjusted under 35 U.S.C. 154(b) by 0 days.

(21) Appl. No.: 13/876,774

(22) PCT Filed: Sep. 30, 2011

(86) PCT No.: PCT/CN2011/001668

§ 371 (c)(1), (2), (4) Date: Apr. 26, 2013

(87) PCT Pub. No.: WO2012/041018

PCT Pub. Date: Apr. 5, 2012

(65) Prior Publication Data

US 2014/0086904 A1 Mar. 27, 2014

(30) Foreign Application Priority Data

Sep. 30, 2010 (CN) .......................... 2010 1 0297255

(51) Int. Cl.

*C07K 16/24* (2006.01)

*A61K 39/00* (2006.01)

(52) U.S. Cl.

CPC ............. *C07K 16/249* (2013.01); *C07K 16/241* (2013.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search

None

See application file for complete search history.

(56) References Cited

FOREIGN PATENT DOCUMENTS

| | | | |
|---|---|---|---|
| CN | 101407546 | A | 4/2009 |
| WO | 2009/132037 | A1 | 10/2009 |
| WO | 2010/105446 | A1 | 9/2010 |

OTHER PUBLICATIONS

PCT International Search Report for PCT Application No. PCT/CN2011/001668 mailed Jan. 19, 2012 (4 pages).

CDP 571:Anti-TNF Monoclonal Antibody, BAY 103356, BAY W 3356, Humicade, Drugs in R&D, 2003, 4(3):174-178.

Esposito et al., "TNF-Alpha as a Therapeutic Target in Inflammatory Diseases, Ischemia-Reperfusion Injury and Trauma," Current Medicinal Chemistry, 2009, 16:3152-3167.

Kupper et al., "Adalimumab," Handbook of Therapeutic Antibodies, 2007, 697-732.

Mazumdar et al., "Golimumab," MABS, Landes Bioscience, US, 2009, 1(5):422-431.

Reinhart et al., "Randomized, Placebo-Controlled Trial of the Anti-Tumor Necrosis Factor Antibody Fragment Afelimomab in Hyperinflammatory Response During Severe Sepsis: The RAMSES Study," Crit. Care Med., 2001, 29 (4):765-769.

Taylor, "Pharmacology of TNF Blockage in Rheumatoid Arthritis and Other Chronic Inflammatory Diseases," Current Opinion in Pharmacology, 2010, 10:308-315.

Tracey et al., "Tumor Necrosis Factor Antagonist Mechanisms of Action: A Comprehensive Review," Pharmacology & Therapeutics, 2008, 117:244-279.

Wiekowski et al., "Infliximab (Remicade)," Handbook of Therapeutic Antibodies, 2007, 885-904.

Supplementary European Search Report for EP Application No. 11 82 7916 mailed Feb. 10, 2014 (11 pages).

*Primary Examiner* — Brian J Gangle

*Assistant Examiner* — Andrea McCollum

(74) *Attorney, Agent, or Firm* — Sutherland Asbill & Brennan LLP

(57) ABSTRACT

The present invention discloses a humanized anti-human tumor necrosis factor-α antibody and antigen-binding fragment (Fab) thereof. The present invention also discloses a composition comprising the said antibody or antigen-binding fragment (Fab) thereof, and the use of the said antibody or antigen-binding fragment (Fab) thereof in treating the diseases associated with tumor necrosis factor-α.

13 Claims, 3 Drawing Sheets

HUMANIZED ANTI-TNF-α ANTIBODY AND ANTIGEN-BINDING FRAGMENT (FAB) THEREOF AND USE OF THE SAME

CROSS REFERENCE TO RELATED APPLICATIONS

This application is a national phase of PCT/CN2011/001668 filed on Sep. 30, 2011, which claims priority of Chinese Application No. 201010297255.0 filed on Sep. 30, 2010. The contents of these applications are hereby incorporated by reference in their entirety.

FIELD OF THE INVENTION

The present invention relates to humanized anti-human tumor necrosis factor-α (TNF-α) antibodies and antigen-binding fragments (Fabs) thereof and use of the same.

SEQUENCE LISTING

The instant application contains a Sequence Listing which has been submitted in ASCII format via EFS-Web and is hereby incorporated by reference in its entirety. Said ASCII copy, created on Nov. 8, 2013, is named 32177-0004_SL.txt and is 62,897 bytes in size.

BACKGROUND OF THE INVENTION

The development and progression of the autoimmune disease is a complex process due to imbalance in regulation of many active cytokines. Tumor necrosis factor-α (TNF-α) has been shown to play an important role in immune regulation among numerous cytokines. However, its overexpression has been demonstrated to be one of the main causes of autoimmune diseases etc. Accordingly, use of biopharmaceuticals suppressing TNF-α activity become one of the most successful therapies for the treatment of such diseases. Indications which have been approved mainly encompass rheumatoid arthritis, Crohn's disease, plaque psoriasis, psoriatic arthritis, ankylosing spondylitis, ulcerative colitis, and juvenile idiopathic arthritis, while a variety of other related diseases are subjected to clinical trials.

Currently, in European and American market, pharmaceutical anti-TNF-α antibodies and antibody-like Fc fusion protein drugs, such as REMICADE® (infliximab), have been available. But REMICADE® has a shorter half-life in vivo of approximately 9 days. In addition, although REMICADE® has good binding affinity, bioactivity, and clinical efficacy, as a chimeric antibody consisting of ⅓ of murine-derived sequences and ⅔ of human-derived sequences, about 10%-47% of patients appear an immune response after administration of REMICADE®, generally resulting in the production of human anti-mouse antibodies (HAMA), which affects the potency and long-term application of the antibody. Accordingly, there is a great need for an anti-TNF-α antibody with higher degree of humanization and maximally reduced proportion of the murine-derived sequences to decrease the degree of murine origin and allow safe usage in treating diseases in human. A common process for humanizing an antibody is to graft parts of the complementary-determining regions (CDRs) of the variable regions ($V_H$, $V_K$) of a murine-derived antibody into the framework regions of a previously selected human antibody. The resultant antibody will consist mostly of human-derived sequences and be able to retain the selectivity of the starting antibody of murine origin for the same antigen. However, the process generally leads to loss of the antibody affinity.

SUMMARY OF THE INVENTION

One object of the present invention is to provide humanized anti-human tumor necrosis factor-α (TNF-α) antibodies and antigen-binding fragments (Fabs) thereof, the affinity of which for human tumor necrosis factor-α is comparable to or even higher than that of REMICADE®, a human-murine chimeric antibody.

The humanized anti-human tumor necrosis factor-α (TNF-α) antibodies or the Fabs provided in the present invention comprises a heavy chain variable region and a light chain variable region, wherein the amino acid sequence of the heavy chain variable region is shown in SEQ ID NO: 1 or 3 in the sequence listing and the amino acid sequence of the light chain variable region is shown in SEQ ID NO: 15, 9, 11, 7, 13 or 5 in the sequence listing, and the first amino acid residue of SEQ ID NO: 1 is Glu or Gln.

The antibody is particularly selected from any one of the following a) to l):

a) KS10, having a heavy chain variable region SH01 with the amino acid sequence shown in SEQ ID NO: 1, and a light chain variable region SH08 with the amino acid sequence shown in SEQ ID NO: 15;

b) KS03, having a heavy chain variable region SH01 with the amino acid sequence shown in SEQ ID NO: 1, and a light chain variable region SH05 with the amino acid sequence shown in SEQ ID NO: 9;

c) KS06, having a heavy chain variable region SH01 with the amino acid sequence shown in SEQ ID NO: 1, and a light chain variable region SH06 with the amino acid sequence shown in SEQ ID NO: 11;

d) KS12, having a heavy chain variable region SH02 with the amino acid sequence shown in SEQ ID NO: 3, and a light chain variable region SH08 with the amino acid sequence shown in SEQ ID NO: 15;

e) KS04, having a heavy chain variable region SH02 with the amino acid sequence shown in SEQ ID NO: 3, and a light chain variable region SH05 with the amino acid sequence shown in SEQ ID NO: 9;

f) KS07, having a heavy chain variable region SH02 with the amino acid sequence shown in SEQ ID NO: 3, and a light chain variable region SH06 with the amino acid sequence shown in SEQ ID NO: 11;

g) KS02, having a heavy chain variable region SH02 with the amino acid sequence shown in SEQ ID NO: 3, and a light chain variable region SH03 with the amino acid sequence shown in SEQ ID NO: 5;

h) KS08, having a heavy chain variable region SH02 with the amino acid sequence shown in SEQ ID NO: 3, and a light chain variable region SH04 with the amino acid sequence shown in SEQ ID NO: 7;

i) KS11, having a heavy chain variable region SH02 with the amino acid sequence shown in SEQ ID NO: 3, and a light chain variable region SH07 with the amino acid sequence shown in SEQ ID NO: 13;

j) KS01, having a heavy chain variable region SH01 with the amino acid sequence shown in SEQ ID NO: 1, and a light chain variable region SH03 with the amino acid sequence shown in SEQ ID NO: 5;

k) KS05, having a heavy chain variable region SH01 with the amino acid sequence shown in SEQ ID NO: 1, and a light chain variable region SH04 with the amino acid sequence shown in SEQ ID NO: 7;

l) KS09, having a heavy chain variable region SH01 with the amino acid sequence shown in SEQ ID NO: 1, and a light chain variable region SH07 with the amino acid sequence shown in SEQ ID NO: 13;
wherein, the first amino acid residue of SEQ ID NO: 1 is Glu or Gln.

Another object of the present invention is to provide a humanized anti-human tumor necrosis factor-α antigen-binding fragment (Fab). The Fab comprises a heavy chain variable region, the amino acid sequence of which corresponds to the positions 1-120 of SEQ ID NO: 27 or SEQ ID NO: 25 in the sequence listing, and a light chain variable region, the amino acid sequence of which corresponds to the positions 1-109 of SEQ ID NO: 31 or SEQ ID NO: 29 in the sequence listing.

The antibody provided in the invention consists of a heavy chain, in which the amino acid sequence of the constant region is identical to that of the human antibody heavy chain, and a light chain, in which the amino acid sequence of the constant region is identical to that of the human antibody light chain.

The heavy chain constant region of the described antibody may be a human-derived constant region of any classes (IgG, IgA, IgM, IgE, IgD) or subclasses (IgG1, IgG2, IgG3, IgG4, IgM1, IgM2, IgA1, IgA2), and the light chain constant region of the described antibody may be a human-derived light chain constant region of any classes (κ or λ) or subclasses (λ1, λ2, λ3, λ4), or allotypes (κm (1), κm (2), κm (3)).

The amino acid sequence of the heavy chain constant region of the antibody is particularly shown in SEQ ID NO: 17 in the sequence listing; and the amino acid sequence of the light chain constant region of the antibody is particularly shown in SEQ ID NO: 19 in the sequence listing.

The amino acid sequence of said heavy chain is shown in SEQ ID NO: 21 in the sequence listing; and the amino acid sequence of said light chain is shown in SEQ ID NO: 23 in the sequence listing. The amino acid residues at positions 1-120 of SEQ ID NO: 21 correspond to the variable region of the heavy chain, and the amino acid residues at positions 121-450 thereof correspond to the constant region of the heavy chain. The amino acid residues at positions 1-109 of SEQ ID NO: 23 correspond to the variable region of the light chain, and the amino acid residues at positions 110-214 thereof correspond to the constant region of the light chain. The first amino acid residue of SEQ ID NO: 21 is Glu or Gln.

The Fab provided in the present invention consists of a heavy chain Fd fragment and a light chain; wherein said heavy chain Fd fragment includes $V_H$ and CH1 and said light chain includes $V_K$ and a light chain constant region; wherein the amino acid sequence of the CH1 is identical to that of the constant region CH1 of human antibody heavy chain, and the amino acid sequence of said light chain constant region is identical to that of the constant region of human antibody light chain.

The CH1 of the Fd fragment of the above Fab could be a human-derived constant region CH1 of any classes (IgG, IgA, IgM, IgE, IgD) or subclasses (IgG1, IgG2, IgG3, IgG4, IgM1, IgM2, IgA1, IgA2); the light chain constant region of the above Fab may be a human-derived light chain constant region of any classes (κ or λ) or subclasses (λ1, λ2, λ3, λ4), or allotypes (κm (1), κm (2), κm (3)).

The amino acid sequence of the CH1 is shown in SEQ ID NO: 33 in the sequence listing; the amino acid sequence of the constant region in said light chain is shown in SEQ ID NO: 19 in the sequence listing.

In particular embodiments of the invention, the Fab is any one of the following b1)-b3):

b1) KS-7F: the amino acid sequence of the heavy chain fragment is shown in SEQ ID NO: 27 in the sequence listing; and the amino acid sequence of the light chain is shown in SEQ ID NO: 31 in the sequence listing;

b2) KS-7A: the amino acid sequence of said heavy chain fragment is shown in SEQ ID NO: 25 in the sequence listing; and the amino acid sequence of said light chain is shown in SEQ ID NO: 31 in the sequence listing;

b3) KS-2E: the amino acid sequence of said heavy chain fragment is shown in SEQ ID NO: 25 in the sequence listing; and the amino acid sequence of said light chain is shown in SEQ ID NO: 29 in the sequence listing.

A still another object of the present invention is to provide antigen-binding fragment A or antigen-binding fragment B, wherein the antigen-binding fragment A is a Fab, a Fab', a $F(ab')_2$, a Fv (variable region fragments of an antibody), a heavy chain variable region, a light chain variable region, polypeptide fragments selected from the heavy chain variable region or polypeptide fragments selected from the light chain variable region, which are derived from the said antibody; and the antigen-binding fragment B is a Fab', a $F(ab')_2$, a Fv, a heavy chain variable region, a light chain variable region, polypeptide fragments selected from the heavy chain variable region or polypeptide fragments selected from the light chain variable region, which are derived from the said Fab.

The above-mentioned $F(ab')_2$ is composed of a pair of light chains and a pair of heavy chains (referred to as Fd') which are slightly larger than Fd. Hydrolysis of IgG molecules by pepsin can produce this $F(ab')_2$ fragment, which comprises two Fabs, and thus could bind to two antigenic epitopes. Fd' comprises about 235 of amino acid residues, encompassing $V_H$, CH1, and a hinge region. Fv consists of a light chain variable region ($V_L$) and a heavy chain variable region ($V_H$), which are associated together via non-covalent bonds. Fv has a molecular weight of about one sixth that of an intact antibody molecule, owning a single antigen-binding site. Fv includes ScFv (single-chain antibodies), DsFv (disulphide-bond stabilized antibodies) etc. ScFv is a single peptide chain expressed from $V_H$ and $V_L$ linked together by a piece of suitable oligonucleotide (a linker). DsFv is a disulphide-bond immobilized Fv fragment formed via respectively introducing one cysteine into light chain and heavy chain variable regions at a proper site. DsFv has been shown to be superior to ScFv in both binding ability and stability.

Also fallen within the claimed scope of the invention is a gene encoding any one of the following proteins A)-C):

A) the said antibody; B) the said Fab; C) the antigen-binding fragment A or B.

The coding sequences of the heavy chain variable regions of both the antibody and the antigen-binding fragment A are shown in SEQ ID NO: 2 or 4 in the sequence listing. The coding sequences of the light chain variable regions of both the antibody and the antigen-binding fragment A are selected from one of SEQ ID NOs: 16, 10, 12, 8, 14, and 6 in the sequence listing. The coding sequences of the heavy chain variable regions of both the Fab and the antigen-binding fragment B correspond to positions 1-360 of any sequence of SEQ ID NOs: 2, 4, 28 and positions 1-360 of SEQ ID NO: 26 in the sequence listing. The coding sequences of the light chain variable regions of both the Fab and the antigen-binding fragment B correspond to positions 1-327 of any sequence of SEQ ID NOs: 16, 10, 12, 8, 14, 6, 32 and positions 1-327 of SEQ ID NO: 30 in the sequence listing.

In above sequences, both SEQ ID NO: 2 and 4 have 360 nucleotides; while all of SEQ ID NO: 6, 8, 14, 10, 12, and 16 have 327 nucleotides.

The coding sequence of the heavy chain constant region of the antibody is shown in SEQ ID NO: 18 in the sequence listing; and the coding sequence of the light chain constant region of the antibody is shown in SEQ ID NO: 20 in the sequence listing.

The coding sequence of the CH1 region of the Fab is shown in SEQ ID NO: 34 in the sequence listing; the coding sequence of the light chain constant region of the Fab is shown in SEQ ID NO: 20 in the sequence listing.

In the embodiment of the present invention, the coding sequence of the heavy chain of the antibody is particularly shown in SEQ ID NO: 22 in the sequence listing; the coding sequence of the light chain of the antibody is particularly shown in SEQ ID NO: 24 in the sequence listing.

The coding sequence of the said Fab is any one of the following c1)-c3):

c1) KS-7F: the coding sequence of the heavy chain fragment of the Fab is shown in SEQ ID NO: 28 in the sequence listing; and the coding sequence of the light chain of the Fab is shown in SEQ ID NO: 32 in the sequence listing;

c2) KS-7A: the coding sequence of the heavy chain fragment of the Fab is shown in SEQ ID NO: 26 in the sequence listing; and the coding sequence of the light chain of the Fab is shown in SEQ ID NO: 32 in the sequence listing;

c3) KS-2E: the coding sequence of the heavy chain fragment of the Fab is shown in SEQ ID NO: 26 in the sequence listing; and the coding sequence of the light chain of the Fab is shown in SEQ ID NO: 30 in the sequence listing.

While the nucleotides at positions 1-360 and 360-1350 of SEQ ID NO: 22 correspond to the mentioned variable region nucleotides of the heavy chain and the constant region nucleotides of the heavy chain, respectively; the nucleotides at positions 1-327 and 328-642 of SEQ ID NO: 24 correspond to the mentioned variable region nucleotides of the light chain and the constant region nucleotides of the light chain, respectively.

A still another object of the present invention is to provide the following genetic materials: a recombinant vector, a recombinant bacterium, a recombinant cell line, a recombinant virus or an expression cassette comprising the gene set forth above.

The recombinant vector is a prokaryotic or eukaryotic expression vector for expressing the antibody, the Fab, or the antigen-binding fragment. The recombinant bacterium is an *Escherichia coli* harboring the gene set forth above. The recombinant cell line is a transgenic cell line or fusion cell line, wherein the transgenic cell line can be a mammal cell line into which said gene encoding the humanized anti-human tumor necrosis factor-α antibody, or Fab, or antigen-binding fragment thereof in the present invention has been transferred, preferably CHO cell line, or 293 cell line and sublines thereof; the fusion cell line is hybridoma cells which can secrete the humanized anti-human tumor necrosis factor-α antibody mentioned in the present invention. The recombinant virus is a recombinant adenovirus or a recombinant adeno-associated virus, etc, which carries the gene set forth above. The expression cassette is a DNA molecule which includes three fragments from upstream to downstream as follows: a promoter; the coding gene of the antibody, or the Fab, or the antigen-binding fragment of which the transcription is initiated by the promoter; and a terminator.

If a host cell is transfected or transformed with a recombinant vector comprising the coding gene of the antibody, the Fab, or the antigen-binding fragment, the corresponding proteins can be expressed, thus obtaining the antibody or Fab, or the antigen-binding fragment. The said host cell may be an eukaryotic cell, and may also be a prokaryotic cell, including, but not limited to a mammal cell, a bacterium, a yeast, an insect cell, etc. There are a wide variety of mammal cells useful for large-scale protein expression, such as 293, CHO, SP20, NS0, COS, BHK, or PerC6 cells, etc. There are various methods for transfecting a cell, including, but not limited to, electroporation, liposome-mediated transfection, calcium phosphate-mediated transfection, etc.

A preferable way for expressing the antibody, the Fab, or the antigen-binding fragment is as follows: performing gene amplification with the recombinant vector in a stably transfected host cell in order to increase the expression level of the recombinant protein. For example, a DHFR-deficient host cell is transfected stably with a recombinant vector comprising a dihydrofolate reductase (DHFR), and then methotrexate (MTX) can be added into the cell culture medium at a concentration sufficient to increase the copy number of the recombinant vector in the host cell.

After the expression of the Fab or IgG comprising the combination of coding gene sequences, an enzyme-linked immunosorbent assay (ELISA) or other assays can be used to determine the concentration of the protein in the culture medium. For the Fab fragments, they can be purified with an affinity chromatography using Protein G; and IgG proteins can be purified with an affinity chromatography using Protein A.

Also fallen within the claimed scope of the invention is the use of the antibody, or the Fab, or the antigen-binding fragment, or the gene, or the genetic material in:

d1) preparation of a medication for preventing and/or treating diseases associated with human tumor necrosis factor-α, or d2) preparation of a product for neutralizing the human tumor necrosis factor-α, or d3) preparation of a kit for qualitatively or quantitatively detecting the human tumor necrosis factor-α.

Wherein the disease associated with human tumor necrosis factor-α is a disease caused by increase in human tumor necrosis factor-α, preferably rheumatoid arthritis, autoimmune uveitis, Crohn's disease, plaque psoriasis, psoriatic arthritis, ankylosing spondylitis, ulcerative colitis, or juvenile idiopathic arthritis.

A still another object of the present invention is to provide a pharmaceutical composition comprising auxiliary materials and active ingredients, wherein the active ingredients includes at least one of the following materials: the antibody, the Fab, the antigen-binding fragment, the gene, and the genetic material set forth above; and the auxiliary material is an pharmaceutically acceptable carrier or excipient. The active ingredients in the pharmaceutical composition may only be any one of the Fabs or antibodies above-mentioned, or any one of the antigen-binding fragments above-mentioned, or any one of the genes above-mentioned, or any one of the genetic materials above-mentioned.

Also fallen within the claimed scope of the invention is the use of any one of the following materials in treatment of diseases associated with human tumor necrosis factor-α: the antibody, the Fab, the antigen-binding fragment, the gene, the genetic material, and the pharmaceutical composition set forth above.

The disease associated with human tumor necrosis factor-α is caused by increase of human tumor necrosis factor-α, preferably autoimmune uveitis, rheumatoid arthritis, Crohn's disease, plaque psoriasis, psoriatic arthritis, ankylosing spondylitis, ulcerative colitis, or juvenile idiopathic arthritis.

DESCRIPTION OF THE ACCOMPANYING DRAWINGS

EXAMPLES

Figure 1:
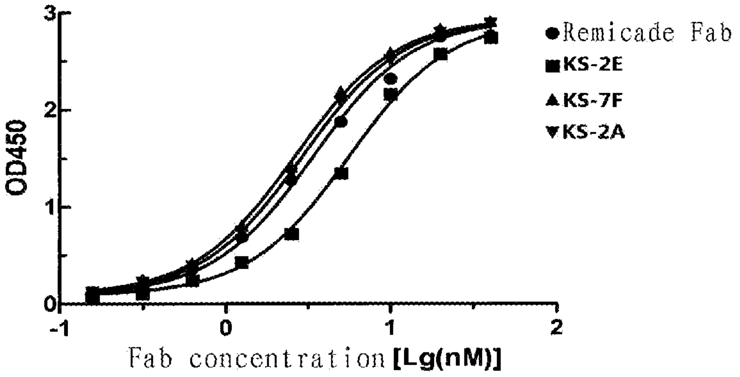
FIG. 1 shows detection of the bioactivity of the humanized Fab in the suppression of TNF-α by ELISA.

The following examples are provided for better understanding of the invention, and not to limit the invention. Unless specially stated, the experimental methods set forth below are all conventional ones. Unless otherwise stated, the experimental materials used in the examples are all purchasable from common shops of biochemical reagents. The quantitative assays in the following examples were performed in triplicate, and the results are the average values.

Grafting of CDRs of the heavy and light chains of a humanized anti-TNF-α antibody, site-directed mutagenesis by PCR, and screening a mutant library described in the invention were accomplished by conventional gene recombination technologies and immunological techniques based on antigen-antibody interaction, and the detailed experimental procedures and steps are documented in "Molecular Cloning: a Laboratory Manual", 3rd edition, by Joseph Sambrook, Science Press, and similar experiment handbooks. $EC_{50}$ in the following examples was obtained by inputting the values of optical density ($OD_{450}$) into the software GraphPad Prism 5, while generating the result graphs.

Example 1

Expression of the Fab of the Humanized Anti-TNF-α Antibody and Detection of its Activity In this example, three Fabs of humanized anti-TNF-α antibodies (the Fab consists of the heavy chain Fd fragment and the light chain of the antibody) are involved, namely, KS-2E, KS-7A, and KS-7F.

1. Construction of Expression Vectors for KS-2E, KS-7A, and KS-7F (1) Obtaining the Sequences of Light and Heavy Chains From mice immunized with human TNF-α (R & D Co., Catalog Number: 210-TA-050), hybridoma cells were obtained and subjected to monoclonal screening, and then total RNA was extracted and used as a template from which the nucleotide sequences for the heavy chain variable region were amplified by PCR using the general primers P1: 5'-GCGAATTCAGGTSMARCTGCAGSAGTCWGG-3' (SEQ ID NO: 40), P2: 5'-TGAGGAGACGGTGACCGTGGTCCCTTGGCCCCAG-3' (SEQ ID NO: 41) and the nucleotide sequences for the light chain variable region were amplified by PCR using the general primers P3: 5'-GACATTCTGMTSACMCAGMCTCC-3' (SEQ ID NO: 42), P4: 5'-GTTAGATCTCGAGCTTGGTCCC-3' (SEQ ID NO: 43). The gel slices comprising the bands of interest were excised for recovery. The amplified products of the light and heavy chains of the antibody were each inserted into the vector pMD18-T (TaKaRa Co., Catalog Number: D101C). The single colonies were separately picked out and sequenced to identify the nucleotide sequences for the heavy and light chains variable regions of the antibody.

(2) Construction of the Humanized Fab

Comparison of amino acid sequence similarity between the resultant light chain variable region and the light chain variable region of a humanized antibody, between the resultant heavy chain variable region and the heavy chain variable region of a humanized antibody were performed. The sequence similarities were searched separately in IgBLAST and IMGT (ImMunoGeneTics). On the basis of the searching results, an antibody with higher sequence similarities to both the light and heavy chains was chosen as the template for the humanized antibody. The resultant heavy chain variable region VH was grafted into the framework region of the human antibody IGHV3-15*07 (Accession number: M99406) having higher sequence similarity, and the resultant light chain variable region VK was grafted into the framework region of the human antibody IGKV6-21*01 (Accession number: X63399) having a higher sequence similarity.

After multiple cycles of mutations in the human original heavy chain fragments (Fd) and light chains, the combinations of various light chains and heavy chain fragments (Fd) were inserted into the vector pTLR (a modified pET22b (+) vector). Specifically, prepare various DNAs for the light chains with the restriction endonuclease sites BamHI and EcoRI respectively at each end, and various DNAs for the heavy chain fragments (Fd) with the restriction endonuclease sites Nod and XhoI respectively at each end. The two groups of DNA were separately cloned into the vector pTLR (a modified pET22b (+) vector) between the corresponding restriction endonuclease sites, that is, various DNAs for the light chains were inserted between the restriction endonuclease sites BamHI and EcoRI, various DNAs for the heavy chain fragments (Fd) were inserted between the restriction endonuclease sites Nod and XhoI, resulting in construction of several Fab expression vectors (including three Fab expression vectors which express KS-2E, KS-7A, and KS-7F, respectively).

Various combinations of the light chains and the heavy chain fragments (Fd) mentioned above include the three Fabs, KS-2E, KS-7F, and KS-7A. The amino acid sequence of the heavy chain fragment of the KS-2E is shown in SEQ ID NO: 25 in the sequence listing, the nucleotide sequence thereof is shown in SEQ ID NO: 26, and the amino acid sequence of the light chain of the KS-2E is shown in SEQ ID NO: 29 in the sequence listing, the nucleotide sequence thereof is shown in SEQ ID NO: 30. The amino acid sequence of the heavy chain fragment of the KS-7A is shown in SEQ ID NO: 25 in the sequence listing, the nucleotide sequence thereof is shown in SEQ ID NO: 26, and the amino acid sequence of the light chain of the KS-7A is shown in SEQ ID NO: 31 in the sequence listing, the nucleotide sequence thereof is shown in SEQ ID NO: 32. The amino acid sequence of the heavy chain fragment of the KS-7F is shown in SEQ ID NO: 27 in the sequence listing, the nucleotide sequence thereof is shown in SEQ ID NO: 28, and the amino acid sequence of the light chain of the KS-7F is shown in SEQ ID NO: 31 in the sequence listing, the nucleotide sequence thereof is shown in SEQ ID NO: 32.

The detailed procedure for modifying the pET22b (+) vector to obtain the above-mentioned pTLR vector was as follows: firstly, a DNA segment (abbreviated to the T-L-R DNA sequence, shown in SEQ ID NO: 35 in the sequence listing) was artificially synthesized, which comprises the sequences of a T7 promoter, a lactose operator, and a ribosomal binding site (RBS), with the restriction endonuclease sites SalI and NotI located at each end; then, pET22b (+) vector (the product from Novage Co., USA) and the T-L-R DNA sequence were digested separately with both SalI and NotI restriction endonucleases, then ligated together by T4 DNA ligase, and transformed; at last, the single colony was picked out by conventional method and sequenced to screen the properly modified vector.

2. Prokaryotic Expression of KS-2E, KS-7A, and KS-7F

The *E. coli* strain Top10 was transformed separately with the constructed Fab expression vectors above-mentioned (including three Fab expression vectors which express KS-2E, KS-7A, and KS-7F, respectively), and then was plated onto a 2-YT plate (peptone 1.6%, yeast extract 1%, NaCl 0.5%, and agar powder 1.5%) with chloramphenicol. Next day, the plate with a suitable colony density was selected to pick out several single colonies. For each positive colony, eight single colonies were picked and put in a 96-well deep well plate and induced with IPTG for expression. Each single colony was added into a tube with 6 ml of 2-YT liquid medium (peptone 1.6%, yeast extract 1%, and NaCl 0.5%) containing chloramphenicol and shaken at 250 rpm and at 37° C. for 12 hours. 0.2 μl of the bacterial suspension was pipetted from each tube and transferred onto the 2-YT plate with chloramphenicol for storage. 5 ml of the bacterial suspension was inoculated into 500 ml of the chloramphenicol-containing 2-YT liquid medium and cultured at 33° C., 300 rmp until $OD_{600}$ reached 0.6. IPTG was then added into the medium to a final concentration of 50 μM, in order to induce the expression of various Fabs with an induction time of 3 hours. After the induced expression was completed, the culture medium was centrifugated at 5100 rpm and 10° C. for 15 minutes. The supernatant was discarded and the bacterial precipitate was resuspended completely with 40 ml of pre-chilled TES solution; 66 ml of pre-chilled TES diluted to 20% with $H_2O$ solution was again added into the resuspended bacterial solution and incubated on ice for 40 minutes, followed by centrifugation at 13000 rpm, 4° C. for 10 minutes. After centrifugation, the supernatant was collected, which is a periplasmic extract containing Fab proteins (KS-2E, KS-7A or KS-7F protein). The periplasmic extract was desalted by passing through a G-25 (GE Co., 17-0034-01)) column. A Protein G (GE Co., 17-0618-04) prepacked column was prepared, equilibrated with an equilibration solution (20 mM phosphate buffer, pH 6.5), and then the protein sample was loaded. After the sample loading, the column was washed with the equilibration solution sequentially, and then eluted directly with an elution solution (0.1 M Gly-HCl, pH 2.5). The eluted fractions were collected and the pH of the eluted fractions was rapidly adjusted to 7.0 by previously adding 1.0 M Tris-HCl buffer (pH 9.0) into the fraction collection tubes before the collection, the volume ratio of the Tris buffer to the eluted fractions was 1:9. The collected liquid comprises the protein of interest. Purity of the protein was assayed by SDS-PAGE and protein concentrations in the protein samples were determined. Finally, the protein sample was subpackaged and stored at −80° C., thus obtaining Fab proteins with higher purity (including three proteins, KS-2E, KS-7A, and KS-7F).

3. Determination of the Bioactivity of KS-2E, KS-7A, and KS-7F

1) Binding Assay of the Humanized Fabs to TNF-α by ELISA

Fab proteins which bind to TNF-α were screened by the following steps: an ELISA plate was coated with 100 ng of human-derived TNF-α (R & D Co., Catalog Number: 210-TA-050) as a substrate per well; a 2-fold serial dilutions of 40 nM of the Fab proteins (prepared in step 2, including three proteins, KS-2E, KS-7A, and KS-7F) were added, and then incubated; a goat anti-human C-Kappa secondary antibody labeled with horseradish peroxidase (Sigma Co., Catalog Number: K3502) was added, and finally TMB was added for development and 2 M sulfuric acid was introduced to stop the reaction, thereby determining the Fab proteins binding to TNF-α. According to such a screening process, three Fabs with higher activity were obtained: KS-2E, KS-7F, and KS-7A, these proteins totally comprises two different VHs (VH01 and VH02, the amino acid sequence of VH01 is shown in SEQ ID NO: 25 and the nucleotide sequence thereof is shown in SEQ ID NO: 26; the amino acid sequence of VH02 is shown in SEQ ID NO: 27 and the nucleotide sequence thereof is shown in SEQ ID NO: 28) and two different VKs (VK03 and VK05, the amino acid sequence of VK03 is shown in SEQ ID NO: 29 and the nucleotide sequence thereof is shown in SEQ ID NO: 30; the amino acid sequence of VK05 is shown in SEQ ID NO: 31 and the nucleotide sequence thereof is shown in SEQ ID NO: 32 (Table 1).

The test result of the binding capacity of the humanized Fab to TNF-α by ELISA was illustrated in FIG. 1. The result indicates that the three humanized Fabs obtained above have an antigen affinity similar to that of the Fab fragment of REMICADE®, a human-murine chimeric antibody, wherein the $EC_{50}$ for binding of KS-7A and KS-7F to the TNF-α is superior to that of the Fab fragment of the human-murine chimeric antibody REMICADE® (table 2).

TABLE 1

Fabs of humanized anti-TNF-α antibodies

| Fab fragment | VH | VK |
|---|---|---|
| KS-2E | VH01 | VK03 |
| N/A | VH02 | VK03 |
| KS-7F | VH01 | VK05 |
| KS-7A | VH02 | VK05 |

Note:
N/A indicates that the Fab fragment was not designated due to the poorer activity.

TABLE 2

$EC_{50}$ for binding of the Fabs of humanized anti-TNF-α antibodies to TNF-α in ELISA assay

| Sample | $EC_{50}$ (nM) |
|---|---|
| REMICADE ® Fab | 3.324 |
| KS-2E | 6.659 |
| KS-7A | 3.027 |
| KS-7F | 2.740 |

Note:
The data in table 2 were the average values of the experiments in triplicate.

2. Detection of the Bioactivity of the Humanized Fabs in the Suppression of TNF-α by a L929 Cytotoxicity Experiment.

Figure 2:
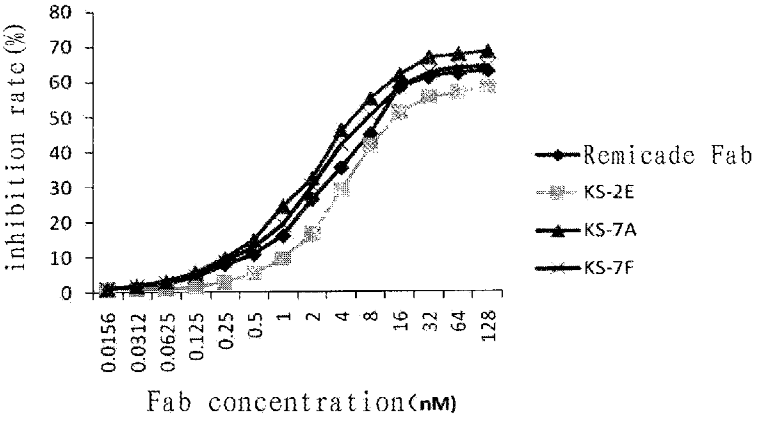
FIG. 2 shows detection of the bioactivity of the humanized Fab in the neutralization of TNF-α by a L929 cytotoxicity experiment.

Furthermore, the bioactivity of the three humanized Fabs above (KS-2E, KS-7F and KS-7A) in the neutralization of TNF-α was verified by a cellular biology experiment, a L929 cytotoxicity assay. In this experiment, $1\times10^4$ L929 cells in logarithmic growth phase were seeded in DMEM (10% FBS, Gibco) media in a 96-well plate. After 24 hours, 0.5 ng/ml TNF-α of human origin (R & D Co., Catalog Number: 210-TA-050) and 0.5 μg/ml actinomycin D (Fluka) were added. The cells were divided into four groups, and the three humanized Fabs mentioned above and the Fab fragment of the control antibody REMICADE® was individually added into each group, the cells were cultured for another 24 hours. Finally, the viability of the cells was analyzed with a CCK8 kit (Dojindo Laboratories). The result is shown in FIG. 2 and indicates that the three humanized Fabs mentioned above can exert the bioactivity of efficaciously neutralizing TNF-α, wherein the bioactivity of KS-7A in the neutralization of TNF-α is superior to that of the Fab fragment of the human-murine chimeric antibody REMICADE®. The data in FIG. 2 are the average values±standard deviation from the experiments performed in triplicate.

Example 2

Construction of an Affinity Maturation Library for the CDR3 of the Fab of the Humanized Anti-TNF-α Antibody In order to further increase the affinity of the Fab fragments of the above-mentioned humanized anti-TNF-α antibody to the antigen, an affinity maturation library was separately constructed for the heavy chain VH02 CDR3 and for the light chain VK05 CDR3 in an expression vector of the humanized anti-TNF-α antibody Fab. Since CDR3 regions of the heavy chain and light chain are the most important region for the binding of an antibody to an antigen, performing a site-saturation mutagenesis on the CDR3 region and then screening may lead to production of an antibody with higher affinity. For the construction of a site-saturation mutagenesis library for the heavy chain and light chain CDR3s, a series of primers for site-directed mutagenesis were designed and used in a PCR reaction. The resultant products amplificated from the PCR reaction were mixed together in an identical degeneracy proportion of the primer series and cloned into the expression vector for the Fab of the humanized anti-TNF-α antibody. Construction of the site-directed mutagenesis library for the light chain CDR3 was performed as follows: performing a PCR with the Primer 5 series and the light chain downstream primer 6 (5'-CGGAATTCCGTACGTTTCACTTCCAGATTGG-3' (SEQ ID NO: 44)) and using a light chain DNA as the template to produce DNA products of interest, then cloning the DNA products into a Fab expression vector, conducting electrotransfer and plating to establish the site-directed mutagenesis library for the light chain CDR3. The Primer 5 series comprise the mutant site in CDR3, and totally include 19 primers listed in Table 3. Construction of the site-directed mutagenesis library for the heavy chain CDR3 was performed as follows: performing a PCR with the mutant Primer 7 series and the heavy chain downstream primer 8 (5'-CCGCTCGAGGCGCTCACGGTCAGGGTGGTGCCCTG-3' (SEQ ID NO: 45)) and using a heavy chain DNA as the template to produce DNA products of interest, then cloning the DNA products into a Fab expression plasmid, conducting electrotransfer and plating to establish the site-directed mutagenesis library for the heavy chain CDR3. The Primer 7 series comprise the mutant site in CDR3, and totally include 22 primers listed in Table 4. From the finally established mutagenesis library for the light and heavy chains, anti-TNF-α antibody Fabs with higher binding capacity to the antigen TNF-α (R & D Co.,) were selected on the basis of the ELISA result. Screening the heavy chain mutants to obtain two heavy chain variable regions with higher activity, namely SH01 and SH02; and screening the light chain mutants to obtain six light chain variable regions with higher activity, namely SH03, SH04, SH05, SH06, SH07 and SH08.

TABLE 3

Primer 5 serials for site-directed mutagenesis in the light chain CDR3

| Designation | Sequence |
|---|---|
| Primer 5-1Q1 | GCAACCTACTACTGC**NBK**CAGAGCCATAGCTGG (SEQ ID NO: 46) |
| Primer 5-1Q2 | GCAACCTACTACTGC**DAK**CAGAGCCATAGCTGG (SEQ ID NO: 47) |
| Primer 5-1Q3 | GCAACCTACTACTGC**CAT**CAGAGCCATAGCTGG (SEQ ID NO: 48) |
| Primer 5-2Q1 | GCAACCTACTACTGCCAG**NBK**AGCCATAGCTGGCCG (SEQ ID NO: 49) |
| Primer 5-2Q2 | GCAACCTACTACTGCCAG**DAK**AGCCATAGCTGGCCG (SEQ ID NO: 50) |
| Primer 5-2Q3 | GCAACCTACTACTGCCAG**CAT**AGCCATAGCTGGCCG (SEQ ID NO: 51) |
| Primer 5-3S1 | GCAACCTACTACTGCCAGCAG**BDK**CATAGCTGGCCGTTC (SEQ ID NO: 52) |
| Primer 5-3S2 | GCAACCTACTACTGCCAGCAG**VCT**CATAGCTGGCCGTTC (SEQ ID NO: 53) |
| Primer 5-3S3 | GCAACCTACTACTGCCAGCAG**AWK**CATAGCTGGCCGTTC (SEQ ID NO: 54) |
| Primer 5-4H1 | GCAACCTACTACTGCCAGCAGAGC**NBK**AGCTGGCCGTTCACC (SEQ ID NO: 55) |
| Primer 5-4H2 | GCAACCTACTACTGCCAGCAGAGC**DAK**AGCTGGCCGTTCACC (SEQ ID NO: 56) |
| Primer 5-4H3 | GCAACCTACTACTGCCAGCAGAGC**CAG**AGCTGGCCGTTCACC (SEQ ID NO: 57) |

TABLE 3-continued

Primer 5 serials for site-directed mutagenesis in the light chain CDR3

| Designation | Sequence |
|---|---|
| Primer 5-5S1 | GCAACCTACTACTGCCAGCAGAGCCAT**BDK**TGGCCGTTCACCTTC (SEQ ID NO: 58) |
| Primer 5-5S2 | GCAACCTACTACTGCCAGCAGAGCCAT**VCT**TGGCCGTTCACCTTC (SEQ ID NO: 59) |
| Primer 5-5S3 | GCAACCTACTACTGCCAGCAGAGCCAT**AWK**TGGCCGTTCACCTTC (SEQ ID NO: 60) |
| Primer 5-6W1 | GCAACCTACTACTGCCAGCAGAGCCATAGC**HNK**CCGTTCACCTTCGGC (SEQ ID NO: 61) |
| Primer 5-6W2 | GCAACCTACTACTGCCAGCAGAGCCATAGC**NGT**CCGTTCACCTTCGGC (SEQ ID NO: 62) |
| Primer 5-6P1 | GCAACCTACTACTGCCAGCAGAGCCATAGCTGG**NDK**TTCACCTTCGGCAGC (SEQ ID NO: 63) |
| Primer 5-6P2 | GCAACCTACTACTGCCAGCAGAGCCATAGCTGG**DCT**TTCACCTTCGGCAGC (SEQ ID NO: 64) |

TABLE 4

Primer 7 serials for site-directed mutagenesis in the heavy chain CDR3

| Designation | Sequence |
|---|---|
| Primer 7-1N1 | GTATTACTGCAGCCGT**NBK**TACTACGGCAGCACC (SEQ ID NO: 65) |
| Primer 7-1N2 | GTATTACTGCAGCCGT**BAK**TACTACGGCAGCACC (SEQ ID NO: 66) |
| Primer 7-1N3 | GTATTACTGCAGCCGT**AAA**TACTACGGCAGCACC (SEQ ID NO: 67) |
| Primer 7-2Y1 | GTATTACTGCAGCCGTAAT**NBK**TACGGCAGCACCTACG (SEQ ID NO: 68) |
| Primer 7-2Y2 | GTATTACTGCAGCCGTAAT**VAK**TACGGCAGCACCTACG (SEQ ID NO: 69) |
| Primer 7-3Y1 | GTATTACTGCAGCCGTAATTAC**NBK**GGCAGCACCTACGATTAC (SEQ ID NO: 70) |
| Primer 7-3Y2 | GTATTACTGCAGCCGTAATTAC**VAK**GGCAGCACCTACGATTAC (SEQ ID NO: 71) |
| Primer 7-4G1 | GTATTACTGCAGCCGTAATTACTAC**NHK**AGCACCTACGATTACTG (SEQ ID NO: 72) |
| Primer 7-4G2 | GTATTACTGCAGCCGTAATTACTAC**HGK**AGCACCTACGATTACTG (SEQ ID NO: 73) |
| Primer 7-5S1 | GTATTACTGCAGCCGTAATTACTACGGC**BDK**ACCTACGATTACTGGGC (SEQ ID NO: 74) |
| Primer 7-5S2 | GTATTACTGCAGCCGTAATTACTACGGC**VCT**ACCTACGATTACTGGGC (SEQ ID NO: 75) |
| Primer 7-5S3 | GTATTACTGCAGCCGTAATTACTACGGC**AWK**ACCTACGATTACTGGGC (SEQ ID NO: 76) |
| Primer 7-6T1 | GTATTACTGCAGCCGTAATTACTACGGCAGC**NDK**TACGATTACTGGGCCC (SEQ ID NO: 77) |
| Primer 7-6T2 | GTATTACTGCAGCCGTAATTACTACGGCAGC**BCT**TACGATTACTGGGCCC (SEQ ID NO: 78) |
| Primer 7-7Y1 | GTATTACTGCAGCCGTAATTACTACGGCAGCACC**NBK**GATTACTGGGGCCAGG (SEQ ID NO: 79) |
| Primer 7-7Y2 | GTATTACTGCAGCCGTAATTACTACGGCAGCACC**VAK**GATTACTGGGGCCAGG (SEQ ID NO: 80) |
| Primer 7-8D1 | GTATTACTGCAGCCGTAATTACTACGGCAGCACCTAC**NBK**TACTGGGGCCAGGGC (SEQ ID NO: 81) |

TABLE 4-continued

| Primer 7 serials for site-directed mutagenesis in the heavy chain CDR3 | |
|---|---|
| Designation | Sequence |
| Primer 7-8D2 | GTATTACTGCAGCCGTAATTACTACGGCAGCACCTAC**HAK**TA CTGGGGCCAGGGC (SEQ ID NO: 82) |
| Primer 7-8D3 | GTATTACTGCAGCCGTAATTACTACGGCAGCACCTAC**GAA**TA CTGGGGCCAGGGC (SEQ ID NO: 83) |
| Primer 7-9Y1 | GTATTACTGCAGCCGTAATTACTACGGCAGCACCTACGAT**NB** **K**TGGGGCCAGGGCACC (SEQ ID NO: 84) |
| Primer 7-9Y2 | GTATTACTGCAGCCGTAATTACTACGGCAGCACCTACGAT**VA** **K**TGGGGCCAGGGCACC (SEQ ID NO: 85) |

Example 3

Expression of the High-Affinity Fab of the Humanized Anti-TNF-α Antibody and the Activity Assay This example relates to two humanized anti-TNF-α antibody Fabs with the designations of FA01 and FA02 respectively. The amino acid sequence of the light chain variable region of FA01 is shown in SEQ ID NO: 15 in the sequence listing (the nucleotide sequence thereof is shown in SEQ ID NO: 16 in the sequence listing), the amino acid sequence of the light chain constant region thereof is shown in SEQ ID NO: 19 in the sequence listing (the nucleotide sequence thereof is shown in SEQ ID NO: 20 in the sequence listing), the amino acid sequence of the heavy chain variable region of heavy chain Fd fragment thereof is shown in SEQ ID NO: 1 in the sequence listing (the nucleotide sequence thereof is shown in SEQ ID NO: 2 in the sequence listing), the amino acid sequence of heavy chain constant region CH1 thereof is shown in SEQ ID NO: 33 in the sequence listing (the nucleotide sequence thereof is shown in SEQ ID NO: 34 in the sequence listing). The amino acid sequence of the light chain variable region of FA02 is shown in SEQ ID NO: 9 in the sequence listing (the nucleotide sequence thereof is shown in SEQ ID NO: 10 in the sequence listing), the amino acid sequence of the light chain constant region thereof is shown in SEQ ID NO: 19 in the sequence listing (the nucleotide sequence thereof is shown in SEQ ID NO: 20 in the sequence listing), the amino acid sequence of the heavy chain variable region of heavy chain Fd fragment thereof is shown in SEQ ID NO: 1 in the sequence listing (the nucleotide sequence thereof is shown in SEQ ID NO: 2 in the sequence listing), the amino acid sequence of heavy chain constant region CH1 thereof is shown in SEQ ID NO: 33 in the sequence listing (the nucleotide sequence thereof is shown in SEQ ID NO: 34 in the sequence listing).

1. Construction and Expression of the High-Affinity Fab of the Humanized Anti-TNF-α Antibody The process for constructing the two Fabs of the humanized anti-TNF-α antibody was the same as example 1. DNAs encoding the heavy and light chains of the two Fabs of the humanized anti-TNF-α antibody mentioned above were separately inserted into the corresponding sites in the pTLR vector to obtain the expression vectors pFA01Fab for FA01 and pFA02Fab for FA02. Following the protocol set forth in example 1, FA01 and FA02 proteins with higher purity were obtained.

2. Detection of the Bioactivity of the High-Affinity Fabs of the Humanized Anti-TNF-α Antibody By means of the L929 cytotoxicity experiment, the two humanized anti-TNF-α antibody Fabs (FA01 and FA02) mentioned above were analyzed for the bioactivity. The detailed procedure is the same as in example 1. The resultant $OD_{450}$ values were input the software GraphPad Prism 5 to calculate $EC_{50}$. The results are shown in table 5, which indicate that the activities of FA01 and FA02 are more potent than that of the Fab fragment of REMICADE® antibody.

TABLE 5

| Bioactivity of the humanized Fabs in the neutralization of TNF-α | |
|---|---|
| Group | $EC_{50}$ (nM) |
| REMICADE ® Fab | 3.184 |
| FA01 | 2.582 |
| FA02 | 2.870 |

Note:
The data in table 5 were the average values of the experiments in triplicate.

Example 4

Expression of the IgG of the Humanized Anti-TNF-α Antibody and Detection of its Activity 1. Construction of the Recombinant Expression Vector for the Humanized Anti-TNF-α Antibody IgG DNA fragments encoding the two heavy chain Fd fragments (comprising SH01 and SH02 respectively) and six light chains (comprising SH03, SH05, SH04, SH06, SH07 and SH08 respectively) obtained in examples 1 and 2 were mutually combined in a way as shown in table 6, assembled together with the DNA fragment for IgG1 Fc constant region by overlap extension PCR, then inserted into the expression plasmid pcDNA3.1(+) by recombination. CHO cells were transfected with the constructed recombinant expression plasmids and the full-length humanized antibodies were expressed.

The detailed protocol is described as follows: (1) DNA fragments for the light chains were directly inserted into the eukaryotic expression vector pcDNA3.1(+) by recombination. The following primers were designed: 5'-TGA AAGCTTATGGAAATTGTGCTGACTCAGTCTC-3' (SEQ ID NO: 86) (the restriction endonuclease site HindIII being underlined); 5'-AAT CTCGAGTCAACACTCTCCCCTGTTGAAGCT-3' (SEQ ID NO: 87) (the restriction endonuclease site XhoI being underlined) and used in a PCR amplification reaction. The amplified products were double digested with the restriction endonuclease HindIII (R0104L, the product from NEB Co.,) and XhoI (R0146L, the product from NEB Co.,) and ligated with the large fragments of pcDNA3.1(+) which had been double digested with the same enzymes by T4 DNA ligase. (2) DNA fragments for the heavy chains needed to be assembled together with the DNA fragment for IgG1 Fc constant region by overlap extension PCR, and inserted into the pcDNA3.1 (+) by recombination. 5'-ACT GGTACCATGGAGGTGCAGCTGGTGGAGTCTGGGG-3' (SEQ ID NO: 88) (the restriction endonuclease site KpnI being underlined); 5'-GATGGGCCCTTGGTGCTAGCG-GAGCTCACGGTCAGGGTGGTGCCC-3' (SEQ ID NO: 89); 5'-GATGGGCCCTTGGTGCTAGCGGAGCT-CACGGTCAGGGTGGTGCCC-3' (SEQ ID NO: 90); 5'-AAT CTCGAGTCATTTACCCGGAGACAGGGAGAGG-3' (SEQ ID NO: 91) (the restriction endonuclease site XhoI being underlined). The assembled PCR products were double digested with the restriction endonuclease KpnI (R0142L, the product from NEB Co.,) and XhoI (R0146L, the product from NEB Co.,), then inserted into the expression plasmid pcDNA3.1 (+) which had been double digested with the same enzymes by recombination, and identified by restriction analysis and sequencing to obtain the proper recombinants.

The expression vectors for 18 antibodies in table 7 were prepared in accordance to the procedure described above. All of DNA sequences encoding the heavy chain variable regions of KS01 (Glu), KS03 (Glu), KS05 (Glu), KS06 (Glu), KS09 (Glu), and KS10 (Glu) are shown in SEQ ID NO: 2 in the sequence listing (the nucleotide sequence at positions 1-3 being GAG) and encode the heavy chain variable regions shown in SEQ ID NO: 1 (the first amino acid being Glu); all of DNA sequences encoding the heavy chain variable regions of KS01 (Gln), KS03 (Gln), KS05 (Gln), KS06 (Gln), KS09 (Gln), and KS10 (Gln) are shown in SEQ ID NO: 2 in the sequence listing, wherein the nucleotide sequence at position 1-3 has been substituted with CAG, and encode the heavy chain variable regions shown in SEQ ID NO: 1 (the first amino acid being Gln); all of DNA sequences encoding the heavy chain variable regions of KS02, KS04, KS07, KS08, KS11, and KS12 are shown in SEQ ID NO: 4 in the sequence listing and encode the heavy chain variable regions as shown in SEQ ID NO: 3; all of DNA sequences encoding the light chain variable regions of KS01 (Glu), KS01 (Gln) and KS02 are shown in SEQ ID NO: 6 in the sequence listing and encode the light chain variable regions shown in SEQ ID NO: 5; all of DNA sequences encoding the light chain variable regions of KS03 (Glu), KS03 (Gln) and KS04 are shown in SEQ ID NO: 10 in the sequence listing and encode the light chain variable regions shown in SEQ ID NO: 9; all of DNA sequences encoding the light chain variable regions of KS05 (Glu), KS05 (Gln) and KS08 are shown in SEQ ID NO: 8 in the sequence listing and encode the light chain variable regions as shown in SEQ ID NO: 7; all of DNA sequences encoding the light chain variable regions of KS06 (Glu), KS06 (Gln) and KS07 are shown in SEQ ID NO: 12 in the sequence listing and encode the light chain variable regions shown in SEQ ID NO: 11; all of DNA sequences encoding the light chain variable regions of KS09 (Glu), KS09 (Gln) and KS11 are shown in SEQ ID NO: 14 in the sequence listing and encode the light chain variable regions shown in SEQ ID NO: 13; all of DNA sequences encoding the light chain variable regions of KS10 (Glu), KS10 (Gln) and KS12 are shown in SEQ ID NO: 16 in the sequence listing and encode the light chain variable regions shown in SEQ ID NO: 15. DNA sequence encoding the heavy chain constant region of the eighteen antibodies is shown in SEQ ID NO: 18 in the sequence listing and encodes the heavy chain constant region shown in SEQ ID NO: 17; DNA sequence encoding the light chain constant region of the eighteen antibodies is shown in SEQ ID NO: 20 in the sequence listing and encodes the light chain constant region shown in SEQ ID NO: 19.

2. Expression and Purification of the Full-Length Humanized Anti-TNF-α IgG Antibody The light chain recombinant plasmids and the heavy chain recombinant plasmids obtained in Step 1 were co-transfected into CHO cells to express the full-length humanized antibodies. After the corresponding plasmids in the combination as shown in table 6 were co-transfected stably into CHO cells respectively by a conventional method, twelve of the corresponding recombinant full-length antibodies were secreted into the supernatant of the cell culture. The supernatant was purified to obtain the corresponding full-length IgG antibody. The detailed steps of purification are as follows:

1) Chromatographic filler

MABSELECT SURE™ (the product from GE Co.,), SUPERDEX® 200 (the product from GE Co.,)

2) Buffer

Affinity equilibration buffer (PBS): 0.2 M sodium hydrogen phosphate: 82.5 mL/L; 0.2 M sodium dihydrogen phosphate: 17.5 mL/L; 2M sodium chloride: 75 mL/L; add ultrapure water, stir fully and mix well, adjust pH with 1 M sodium hydroxide or 1M hydrogen chloride to 7.1-7.3.

Affinity elution buffer: NaCl 2.922 g/L, sodium acetate anhydrous 0.49 g/L, add 2.9 mL/L glacial acetic acid, pH 3.4-3.6.

Affinity regeneration buffer: 5.8 mL/L glacial acetic acid, pH 3.0.

Affinity Clean in-place (CIP) buffer: 1M sodium hydroxide 100 mL/L.

Gel filtration chromatography solution (PBS): 0.2 M sodium hydrogen phosphate: 82.5 mL/L; 0.2 M sodium dihydrogen phosphate: 17.5 mL/L; 2M sodium chloride: 75 mL/L; add ultrapure water, stir fully and mix well, adjust pH with 1 M sodium hydroxide or 1M hydrogen chloride to 6.8.

3) Preparation of the Sample (Clarifying Filtration)

Centrifugation: the sample was centrifugated at 5000-6000 rpm for 10-15 minutes.

Filtration: after centrifugation, the supernatant from the sample was filtered with the H7 (0.45+0.2 μm) filter.

4) Affinity Chromatography

Install the AKTA purification system and an affinity chromatography column (MABSELECT® or MABSELECT SURE™). Wash with 2 column volumes of ultrapure water. Wash with 5 column volumes of affinity equilibration buffer until the baseline is stable, and inject the sample. After the injection of sample, wash with 5-10 column volumes of affinity equilibration buffer. Then the column was eluted with affinity elution buffer, fractions corresponding to the major absorbance peak at 280 nm were collected, eluted with 1 column volume sequentially. The column was eluted with 3 column volumes of affinity regeneration buffer. Wash with affinity equilibration buffer to a neutral pH. Clean in-place with 5 column volumes of MABSELECT® CIP buffer or MABSELECT SURE™ CIP buffer. Wash with 3 column volumes of affinity equilibration buffer until the baseline is stable. Wash with 3 column volumes of ultrapure water until the baseline is stable. Wash with 3 column volumes of 20% ethanol, and store the affinity chromatography column.

5) Gel Filtration Chromatography

Install the AKTA explorer purification system and a SUPERDEX® 200 gel filtration chromatography column. Adjust the flow rate to 5 ml/min, wash with 1 column volume of ultrapure water, and wash with 2 column volumes of SUPERDEX® 200 column chromatography equilibration solution. Adjust the flow rate to 2.5 ml/min, the collected fractions corresponding to affinity chromatography peaks were subjected to pH value adjustment and injected directly onto the column. After sample injection, elute the column with the SUPERDEX® 200 column chromatography equilibration solution, and collect the interest peak at 280 nm. Continue to wash with 1 column volume. The chromatographic column was stored with 0.01 M NaOH.

3. Detection of the Activity of the Humanized Anti-TNF-α Antibody IgG 12 humanized anti-TNF-α antibodies IgG obtained in step 2 were tested for their bioactivity of neutralizing TNF-α by the L929 cytotoxicity experiment (the detailed manipulation was described in example 1), the resultant $OD_{450}$ values were obtained and input the software GraphPad Prism 5 to calculate $EC_{50}$. $EC_{50}$ values of the twelve humanized anti-TNF-α antibody IgG for suppressing the bioactivity of TNF-α were shown in table 7. The results indicate that the bioactivities of the humanized anti-TNF-α antibodies are considerably increased and the KS10 has the highest bioactivity. Thus, a further investigation of antibody activity was carried out largely on KS10.

TABLE 6

High-affinity humanized anti-TNF-α antibody

| IgG antibody | VH | VK |
|---|---|---|
| KS01 | SH01 | SH03 |
| KS02 | SH02 | SH03 |
| KS03 | SH01 | SH05 |
| KS04 | SH02 | SH05 |
| KS05 | SH01 | SH04 |
| KS06 | SH01 | SH06 |
| KS07 | SH02 | SH06 |
| KS08 | SH02 | SH04 |
| KS09 | SH01 | SH07 |
| KS10 | SH01 | SH08 |
| KS11 | SH02 | SH07 |
| KS12 | SH02 | SH08 |

TABLE 7

Bioactivity of the full-length humanized anti-TNF-α antibody in the neutralization of TNF-α

| Group | $EC_{50}$ (nM) |
|---|---|
| KS01 (Glu) | 0.081 |
| KS01 (Gln) | 0.087 |
| KS02 | 0.109 |
| KS03 (Glu) | 0.087 |
| KS03 (Gln) | 0.093 |
| KS04 | 0.126 |
| KS05 (Glu) | 0.051 |
| KS05 (Gln) | 0.064 |
| KS06 (Glu) | 0.059 |
| KS06 (Gln) | 0.068 |
| KS07 | 0.100 |
| KS08 | 0.113 |
| KS09 (Glu) | 0.036 |
| KS09 (Gln) | 0.032 |
| KS10 (Glu) | 0.028 |
| KS10 (Gln) | 0.025 |
| KS11 | 0.059 |
| KS12 | 0.136 |
| REMICADE ® | 0.174 |

Example 5

Kinetic Assay of KS10 (Glu) Binding to hTNF-α hTNF-α (R & D Co., 210-TA-050) and NHS-LCLC-biotin (Catalog Number: 21338, purchased from Thermo-fisher Co.,) were mixed uniformly at a molar ratio of 1:3 and kept at room temperature for 1 hour. Then, the remaining NHS-LCLC-biotin was removed by a PD-10 desalting column (Catalog Number: 17-0851-01, purchased from GE Co.,). The final conjugate products obtained were 50 μg/ml of biotin-hTNF-α.

The kinetic parameters of KS10 binding to hTNF-α were determined by Octet RED 96 system (ForteBio Co.) in the Octet technology platform, the experimental procedure was configured according to the instruction manual of the instrument. 50 μg/ml biotin-hTNF-α was bound to Streptavidin bio sensor (SA) via Loading; the appropriate range of the antibody concentration was determined by a pilot trial to be as follows: 6000 nM, 2000 nM, 666.7 nM, 222.2 nM, 74.1 nM and 24.7 nM. REMICADE® was used as a positive control and PBS (pH 7.4) was used as a blank control. The result (in table 8) shows that KD value of KS10 is less than that of REMICADE®, which suggests that the affinity of KS10 to hTNF-α is higher than that of the human-murine chimeric antibody REMICADE®.

Figure 3:
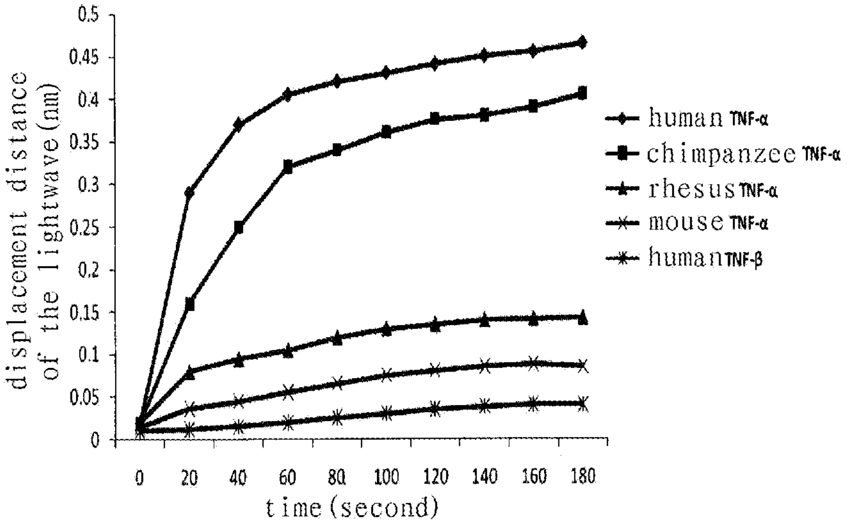
FIG. 3 shows the binding analysis of KS10 to the antigenic TNF-α from different species.

Furthermore, the binding affinity of KS10 to chimpanzee TNF-α (with the amino acid sequence shown in SEQ ID NO: 36 and the nucleotide sequence shown in SEQ ID NO: 37), rhesus TNF-α (with the amino acid sequence shown in SEQ ID NO: 38 and the nucleotide sequence shown in SEQ ID NO: 39), mouse TNF-α (mTNF-α) (Catalog Number: CYT-252, purchased from PROSPEC), and human TNFβ (Catalog Number: CYT-224, purchased from PROSPEC) was determined. According to the affinity evaluation criteria of the Octet RED 96 system, the displacement distance of the lightwave due to binding of an antigen to an antibody reflects indirectly the affinity between the two substances, the longer the displacement distance of the lightwave is, the higher the affinity is. The result (FIG. 3) shows that KS10 binds very strongly to the human TNF-α, also significantly to the chimpanzee TNF-α, weakly to the rhesus TNF-α, rarely to the mouse TNF-α and the human TNFβ. Therefore, it is confirmed that the antibodies provided in the invention have a specific binding ability after humanization.

TABLE 8 kinetic parameters of KS10 binding to hTNF-α

| Class of the antibody | KD (M) | kon (l/Ms) | kdis (l/s) |
|---|---|---|---|
| REMICADE ® | 8.12E−12 | 1.95E+04 | 1.58E−07 |
| KS10 | 2.18E−12 | 4.69E+04 | 1.02E−07 |

Note:
KD is the affinity constant; kon is the binding constant; and kdis is the dissociation constant.

Example 6

Effect of KS10 (Glu) on the Human TNF-α-Induced Rat Model of Rheumatoid Arthritis Seventy-two Sprague Dawley rats (laboratory animal license: SCXK (Sichuan) 2008-24) of 4-6 weeks old, SPF grade, half male and half female, and body weight of 140-180 g were used. The rats were acclimated for one week and then randomized into six groups with 12 rats per group, namely, normal group, negative control group, model control group, 5 mg/kg group of KS10, 10 mg/kg group of KS10, and 20 mg/kg group of KS10. At the beginning of the experiment, rats in each group were anaesthetized with 10% chloral hydrate (350 mg/kg), except the ones in the normal group. Before modeling, the rats in the dose groups were administered by tail vein injection with three different doses of KS10 (5 mg/kg, 10 mg/kg and 20 mg/kg), and the rats in the negative control group and model control group were injected by tail vein with equal volumes of physiologic saline. Fifteen minutes later, 0.5 mg/ml hTNF-α (R & D Co., Catalog Number: 210-TA-050) (dissolved with 1% BSA, with an injection volume of 60 μl/rat) was injected with a 1 ml syringe into the joint cavity of the left ankle of the rats in the three KS10 dose groups and the model control group to induce acute arthritis (modeling of the single foot) and an equal volume of 1% BSA was injected into the joint cavity of the left ankle of the rats in the negative control group. Successful injection was indicated by gradual swelling of the bilateral depressions of the joint cavity. The rats in the normal group were not subjected to the above-mentioned injection.

18 hours after the model was established, the degree of swelling at the left ankle joint of the rats in each group were scored individually in accordance with an modified gradation criteria of 0-4 as follows: 0: no redness and swelling; 1: redness and/or swelling only at the ankle joint; 2: redness and swelling at the ankle joint and swelling at plantar; 3: redness and swelling at the ankle joint and plantar; 4: redness and swelling at the ankle joint, plantar and the surface of foot [Reference: R O Williams, M Feldmann, and R N Maini. Anti-tumor necrosis factor ameliorates joint disease in murine collagen-induced arthritis. Proc Natl Acad Sci USA. 1992 Oct. 15; 89 (20): 9784-9788]. 20 hours after the model was established, joint synovial fluid was drawn. The soft tissues around the joint were separated, homogenized, centrifugated and froze together at −70° C. The levels of IL-1β and IL-6 were determined with a rat ELISA kit (IL-1β being purchased from R & D Co., Catalog Number: RLB00; IL-6 being purchased from R & D Co., Catalog Number: R6000B).

Figure 4:
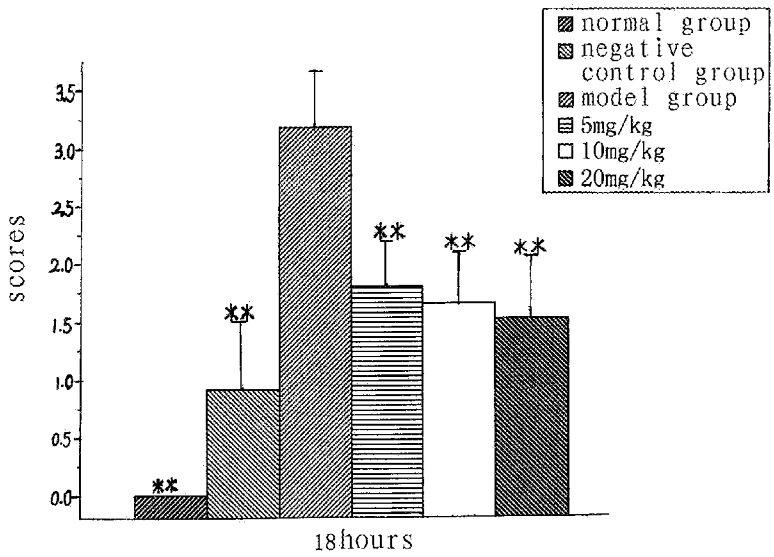
FIG. 4 shows the scores for treatment of the experimental rats having rheumatoid arthritis with KS10. From left to right, there is the normal group, the negative group, the model group, the KS10 5 mg/kg group, the KS10 10 mg/kg group, and the KS10 20 mg/kg group.
Figure 5:
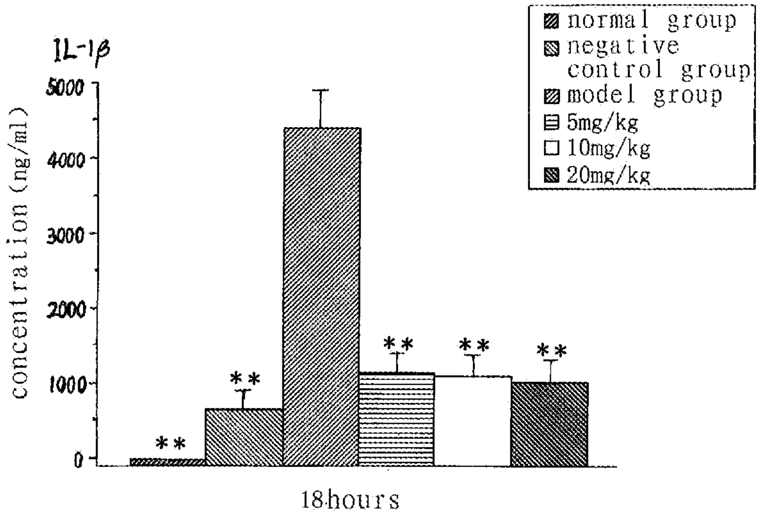
FIG. 5 shows the effect of KS10 on the IL-1β levels in articular synovial fluid/tissues of the experimental rats with rheumatoid arthritis. From left to right, there is the normal group, the negative group, the model group, the KS10 5 mg/kg group, the KS10 10 mg/kg group, and the KS10 20 mg/kg group.
Figure 6:
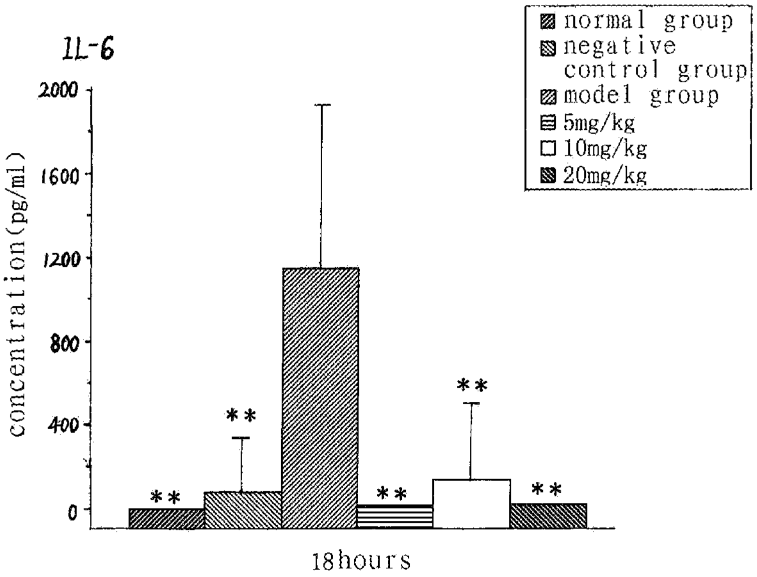
FIG. 6 shows the effect of KS10 on the IL-6 levels in articular synovial fluid/tissues of the experimental rats with rheumatoid arthritis. From left to right, there is the normal group, the negative group, the model group, the KS10 5 mg/kg group, the KS10 10 mg/kg group, and the KS10 20 mg/kg group.

According to the scores (FIG. 4), it is shown that the three dosages of KS10 can alleviate significantly the hTNF-α-induced redness and swelling of the joints of the rats and antagonize significantly the development of the hTNF-α-induced rheumatoid arthritis. It is shown in the cytokine assay that the three dosages of KS10 can lower significantly the levels of IL-1β (FIG. 5) and IL-6 (FIG. 6) in the synovial fluid and in the soft tissues around the joint, which indicates that KS10 can block completely the increased levels of IL-1β and IL-6 induced by TNF-α and serves as the direct evidence for the anti-human TNF-α action of KS10.

Example 7

Treatment Effect of KS10 (Glu) on the Human TNF-α-Induced Rat Model of Uveitis 40 healthy lewis rats were randomized into the normal group, the model group, the negative control group, and the KS10 group. The rats were injected intraperitoneally with 10% chloral hydrate (a dosage of 0.35 ml/kg). After the rats were anaesthetized, 10 μl of physiologic saline was injected (using a 30 G½ needle) into the vitreous through the flat part of the ciliary muscle of each rat in the model and the negative control groups, 10 μl of KS10 solution at a concentration of 4 mg/ml (formulated with PBS) was injected in the same way into each rat in the KS10 group. Thirty minutes later, 10 μl of hTNF-α (about 0.5 mg/ml) was injected intravitreously into each rat in the model and KS10 groups, and 10 μl of 1% BSA was injected intravitreously into each rat in the negative control group. 24 hours and 48 hours after the model was established by the first administration, the rats were anaesthetized, observed under a slit lamp, and scored respectively. The scoring criteria was referred to the literature [Fleisher L N, Ferrell J B, Smith M G, McGahan M C. Lipid mediators of tumor necrosis factor-α-induced uveitis. Invest Ophthalmol V is Sci. 1991 July; 32 (8): 2393-9.] and moderately revised: 0-2: iris hyperaemia 0-2 (0: no hyperaemia, 1: slight hyperaemia; 2: severe hyperaemia); contracted pupil 0-1 (0: normal pupil; 1: contracted pupil); anterior chamber exudation 0-2 (0: no exudation of anterior chamber; 1: slight exudation of anterior chamber; 2: severe exudation of anterior chamber), caligo pupillae or posterior synechia 0-2 (0: no synechia; 1: synechia at either site; 2: synechia at both sites).

The scoring result is shown in table 9 and indicates that KS10 can significantly lower the score of the uveitis evaluation criteria, which is represented by suppressing iris hyperaemia, fibrin exudation, and caligo pupillae or posterior synechia, increasing intraocular transparency. Thus, it has been shown that KS10 exerts a significant antagonistic effect on the hTNF-α-induced uveitis.

TABLE 9

Scores of KS10 for treating the human TNF-α-induced uveitis in the rat model

| | Time after the model was established by the first administration | |
|---|---|---|
| Group | 24 h | 48 h |
| Normal | 0.88 ± 0.834 | 0.38 ± 0.518 |
| Negative | 0.90 ± 0.737 | 0.38 ± 0.744 |
| Model | 3.5 ± 0.971 | 3.78 ± 1.202 |
| KS10 | 2.5 ± 0.971* | 1.55 ± 2.422* |

Note:

*indicates *P < 0.05, compared to the model group ($\overline{X}$ ± SD, n = 10)

INDUSTRIAL APPLICATION

By the mutagenesis of a CDR-grafted antibody, the present invention effectively overcomes the defect that the affinity of an antibody is impaired by the conventional method for humanizing an antibody (in which the complementary determinant region (CDR) of a murine-derived antibody variable region (VH, VK) is directly grafted into the framework region of a human antibody), finally obtains a humanized antibody similar to the initial antibody. The Fabs and IgG antibodies provided in the present invention have a considerably increased degree of humanization (up to over 95%) and are confirmed experimentally to have an affinity and bioactivity similar to or even higher than that of the human-murine chimeric antibody REMICADE®, better neutralizing effect on human TNF-α, and be more efficacious in treating the diseases associated with TNF-α, preferably rheumatoid arthritis, autoimmune uveitis, Crohn's disease, plaque psoriasis, psoriatic arthritis, ankylosing spondylitis, ulcerative colitis, or juvenile idiopathic arthritis.

The invention claimed is:

1. A humanized anti-human tumor necrosis factor-α antibody or antigen-binding fragment Fab thereof, comprising a heavy chain variable region and a light chain variable region, wherein the amino acid sequence of the heavy chain variable region is set forth in SEQ ID NO: 1 or 3; and the amino acid sequence of the light chain variable region is set forth in any one of SEQ ID NO: 15, 9, 11, 7, 13, or 5, and wherein the first amino acid residue of SEQ ID NO: 1 is Glu or Gln.

2. The antibody of claim 1, characterized in that said antibody is any one of the following:

a) KS10, having a heavy chain variable region SH01 with the amino acid sequence as set forth in SEQ ID NO: 1, and a light chain variable region SH08 with the amino acid sequence as set forth in SEQ ID NO: 15;

b) KS03, having a heavy chain variable region SH01 with the amino acid sequence as set forth in SEQ ID NO: 1, and a light chain variable region SH05 with the amino acid sequence as set forth in SEQ ID NO: 9;

c) KS06, having a heavy chain variable region SH01 with the amino acid sequence as set forth in SEQ ID NO: 1, and a light chain variable region SH06 with the amino acid sequence as set forth in SEQ ID NO: 11;

d) KS12, having a heavy chain variable region SH02 with the amino acid sequence as set forth in SEQ ID NO: 3, and a light chain variable region SH08 with the amino acid sequence as set forth in SEQ ID NO: 15;

e) KS04, having a heavy chain variable region SH02 with the amino acid sequence as set forth in SEQ ID NO: 3, and a light chain variable region SH05 with the amino acid sequence as set forth in SEQ ID NO: 9;

f) KS07, having a heavy chain variable region SH02 with the amino acid sequence as set forth in SEQ ID NO: 3, and a light chain variable region SH06 with the amino acid sequence as set forth in SEQ ID NO: 11;

g) KS02, having a heavy chain variable region SH02 with the amino acid sequence as set forth in SEQ ID NO: 3, and a light chain variable region SH03 with the amino acid sequence as set forth in SEQ ID NO: 5;

h) KS08, having a heavy chain variable region SH02 with the amino acid sequence as set forth in SEQ ID NO: 3, and a light chain variable region SH04 with the amino acid sequence as set forth in SEQ ID NO: 7;

i) KS11, having a heavy chain variable region SH02 with the amino acid sequence as set forth in SEQ ID NO: 3, and a light chain variable region SH07 with the amino acid sequence as set forth in SEQ ID NO: 13;

j) KS01, having a heavy chain variable region SH01 with the amino acid sequence as set forth in SEQ ID NO: 1, and a light chain variable region SH03 with the amino acid sequence as set forth in SEQ ID NO: 5;

k) KS05, having a heavy chain variable region SH01 with the amino acid sequence as set forth in SEQ ID NO: 1, and a light chain variable region SH04 with the amino acid sequence as set forth in SEQ ID NO: 7;

l) KS09, having a heavy chain variable region SH01 with the amino acid sequence as set forth in SEQ ID NO: 1, and a light chain variable region SH07 with the amino acid sequence as set forth in SEQ ID NO: 13; and wherein the first amino acid residue of SEQ ID NO: 1 is Glu or Gln.

3. The antibody of claim 1, characterized in that said antibody consists of a heavy chain in which the amino acid sequence of the constant region is identical to that of the heavy chain constant region of a human antibody, and a light chain in which the amino acid sequence of the constant region is identical to that of the light chain constant region of a human antibody.

4. The antibody of claim 3, characterized in that the amino acid sequence of the constant region in said heavy chain is set forth in SEQ ID NO: 17, and the amino acid sequence of the constant region in said light chain is set forth in SEQ ID NO: 19.

5. The antibody of claim 3, characterized in that the amino acid sequence of said heavy chain is set forth in SEQ ID NO: 21, and the amino acid sequence of said light chain is set forth in SEQ ID NO: 23, and wherein the first amino acid residue of SEQ ID NO: 21 is Glu or Gln.

6. The Fab of claim 1, characterized in that said Fab consists of a heavy chain fragment consisting of said heavy chain variable region and a heavy chain constant region CH1, and a light chain consisting of said light chain variable region and a light chain constant region, wherein the amino acid sequence of said CH1 is identical to that of the constant region CH1 of a human antibody heavy chain, and the amino acid sequence of said light chain constant region is identical to that of the constant region of human antibody light chain.

7. The Fab of claim 6, characterized in that the amino acid sequence of said CH1 is set forth in SEQ ID NO: 33, and the amino acid sequence of the constant region in said light chain is set forth in SEQ ID NO: 19.

8. A humanized anti-human tumor necrosis factor-α antigen-binding fragment Fab, comprising a heavy chain variable region and a light chain variable region, wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29.

9. The Fab of claim 8, characterized in that said Fab consists of a heavy chain fragment consisting of said heavy chain variable region and a heavy chain constant region CH1, and a light chain consisting of said light chain variable region and a light chain constant region, wherein the amino acid sequence of said CH1 is identical to that of the constant region CH1 of a human antibody heavy chain, and the amino acid sequence of said light chain constant region is identical to that of the constant region of a human antibody light chain.

10. The Fab of claim 9, characterized in that the amino acid sequence of said CH1 is set forth in SEQ ID NO: 33, and the amino acid sequence of the constant region in said light chain is set forth in SEQ ID NO: 19.

11. The Fab of claim 10, characterized in that the Fab is any one of the following:

KS-7F: the amino acid sequence of said heavy chain fragment is set forth in SEQ ID NO: 27, and the amino acid sequence of said light chain is set forth in SEQ ID NO: 31, KS-7A: the amino acid sequence of said heavy chain fragment is set forth in SEQ ID NO: 25, and the amino acid sequence of said light chain is set forth in SEQ ID NO: 31, and KS-2E: the amino acid sequence of said heavy chain fragment is set forth in SEQ ID NO: 25, and the amino acid sequence of said light chain is set forth in SEQ ID NO: 29.

12. A antigen-binding fragment A derived from any one of the antibodies designated as (a), (b), (c) or (d) as follows or a antigen-binding fragment B derived from the any one of the Fabs designated as (a), (e), (f), (g), (h), (i) or (j) as follows, characterized in that the antigen-binding fragment A is a Fab, a Fab', a $F(ab')_2$, Fv, a heavy chain variable region, a light chain variable region, polypeptide fragments selected from the heavy chain variable region or polypeptide fragments selected from the light chain variable region; the antigen-binding fragment B is a Fab', a $F(ab')_2$, Fv, a heavy chain variable region, a light chain variable region, polypeptide fragments selected from the heavy chain variable region or polypeptide fragments selected from the light chain variable region:

(a) A humanized anti-human tumor necrosis factor-α antibody or antigen-binding fragment Fab thereof, comprising a heavy chain variable region and a light chain variable region, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(b) A humanized anti-human tumor necrosis factor-α antibody, said antibody consists of a heavy chain and a light chain, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln, and wherein the amino acid sequence of the constant region of the heavy chain is identical to that of the heavy chain constant region of a human antibody, and the amino acid sequence of the constant region of the light chain is identical to that of the light chain constant region of a human antibody;

(c) A humanized anti-human tumor necrosis factor-α antibody, said antibody consists of a heavy chain and a light chain, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln, and wherein the amino acid sequence of the constant region in said heavy chain is set forth in SEQ ID NO: 17, and the amino acid sequence of the constant region in said light chain is set forth in SEQ ID NO: 19;

(d) A humanized anti-human tumor necrosis factor-α antibody, said antibody consists of a heavy chain and a light chain, wherein the amino acid sequence of said heavy chain is set forth in SEQ ID NO: 21, and the amino acid sequence of said light chain is set forth in SEQ ID NO: 23, and wherein the first amino acid residue of SEQ ID NO: 21 is Glu or Gln;

(e) A humanized anti-human tumor necrosis factor-α antigen-binding fragment Fab, comprising a heavy chain variable region and a light chain variable region, wherein the amino acid sequence of the heavy chain variable region corresponds to positions 1-120 of SEQ ID NO: 27 or positions 1-120 of SEQ ID NO: 25, and wherein the amino acid sequence of the light chain variable region corresponds to positions 1-109 of SEQ ID NO: 31 or positions 1-109 of SEQ ID NO: 29;

(f) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is identical to that of the constant region CH1 of a human antibody heavy chain, and the amino acid sequence of said light chain constant region is identical to that of the constant region of a human antibody light chain, and wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(g) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is identical to that of the constant region CH1 of a human antibody heavy chain, and the amino acid sequence of said light chain constant region is identical to that of the constant region of a human antibody light chain; and wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29;

(h) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is set forth in SEQ ID NO: 33, and the amino acid sequence of the constant region in said light chain is set forth in SEQ ID NO: 19, and the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(i) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is set forth in SEQ ID NO: 33, and the amino acid sequence of the constant region in said light chain is set forth in SEQ ID NO: 19, and wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29;

(j) A humanized anti-human tumor necrosis factor-α antigen-binding fragment Fab, said Fab consists of a heavy chain fragment and a light chain, the Fab is any one of the following KS-7F: the amino acid sequence of said heavy chain fragment is set forth in SEQ ID NO: 27, and the amino acid sequence of said light chain is set forth in SEQ ID NO: 31; KS-7A: the amino acid sequence of said heavy chain fragment is set forth in SEQ ID NO: 25, and the amino acid sequence of said light chain is set forth in SEQ ID NO: 31; KS-2E: the amino acid sequence of said heavy chain fragment is set forth in SEQ ID NO: 25, and the amino acid sequence of said light chain is set forth in SEQ ID NO: 29.

13. A pharmaceutical composition, comprising auxiliary materials and active ingredients, wherein the active ingredients include at least one of the following materials: any one of the antibodies designated as (a), (b), (c) or (d) as follows, or any one of the Fabs designated as (a), (e), (f), (g), (h), (i) or (j) as follows, or the antigen-binding fragment A derived from the any one of the antibodies designated as (a), (b), (c) or (d) as follows, or the antigen-binding fragment B derived from the any one of the Fabs designated as (a), (e), (f), (g), (h), (i) or (j) as follows, and wherein the auxiliary material is a pharmaceutically acceptable carrier or excipient;

(a) A humanized anti-human tumor necrosis factor-α antibody or antigen-binding fragment Fab thereof, comprising a heavy chain variable region and a light chain variable region, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(b) A humanized anti-human tumor necrosis factor-α antibody, said antibody consists of a heavy chain and a light chain, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln; and wherein the amino acid sequence of the constant region of the heavy chain is identical to that of the heavy chain constant region of a human antibody, and the amino acid sequence of the constant region of the light chain is identical to that of the light chain constant region of a human antibody;

(c) A humanized anti-human tumor necrosis factor-α antibody, said antibody consists of a heavy chain and a light chain, wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln; and wherein the amino acid sequence of the constant region in said heavy chain is set forth in SEQ ID NO: 17, and the amino acid sequence of the constant region in said light chain is set forth in SEQ ID NO: 19;

(d) A humanized anti-human tumor necrosis factor-α antibody, said antibody consists of a heavy chain and a light chain, wherein the amino acid sequence of said heavy chain is set forth in SEQ ID NO: 21, and the amino acid sequence of said light chain is set forth in SEQ ID NO: 23, and wherein the first amino acid residue of SEQ ID NO: 21 is Glu or Gln;

(e) A humanized anti-human tumor necrosis factor-α antigen-binding fragment Fab, comprising a heavy chain variable region and a light chain variable region, wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29;

(f) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is identical to that of the constant region CH1 of a human antibody heavy chain, and the amino acid sequence of said light chain constant region is identical to that of the constant region of a human antibody light chain; and wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(g) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is identical to that of the constant region CH1 of a human antibody heavy chain, and the amino acid sequence of said light chain constant region is identical to that of the constant region of a human antibody light chain; and wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29;

(h) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is set forth in SEQ ID NO: 33, and the amino acid sequence of the constant region in said light chain is set forth in SEQ ID NO: 19; and wherein the amino acid sequence of the heavy chain variable region is set forth in SEQ ID NO: 1 or 3, and the amino acid sequence of the light chain variable region is set forth in any one of SEQ ID NO: 15, 9, 11, 7, 13, and 5, and wherein the first amino acid residue of SEQ ID NO: 1 is Glu or Gln;

(i) A humanized anti-human tumor necrosis factor-α antigen-binding fragment Fab, said Fab consists of a heavy chain fragment consisting of a heavy chain variable region and a heavy chain constant region CH1, and a light chain consisting of a light chain variable region and a light chain constant region, wherein the amino acid sequence of said CH1 is set forth in SEQ ID NO: 33, and the amino acid sequence of the constant region in said light chain is set forth in SEQ ID NO: 19; and wherein the amino acid sequence of the heavy chain variable region corresponds to positions 1-120 of SEQ ID NO: 27 or positions 1-120 of SEQ ID NO: 25, and the amino acid sequence of the light chain variable region corresponds to positions 1-109 of SEQ ID NO: 31 or positions 1-109 of SEQ ID NO: 29;

(j) A humanized anti-human tumor necrosis factor-α antigen-binding fragment Fab, said Fab consists of a heavy chain fragment and a light chain, wherein the Fab is any one of the following: KS-7F: the amino acid sequence of said heavy chain fragment is set forth in SEQ ID NO: 27, and the amino acid sequence of said light chain is set forth in SEQ ID NO: 31; KS-7A: the amino acid sequence of said heavy chain fragment is set forth in SEQ ID NO: 25, and the amino acid sequence of said light chain is set forth in SEQ ID NO: 31; KS-2E: the amino acid sequence of said heavy chain fragment is set forth in SEQ ID NO: 25, and the amino acid sequence of said light chain is set forth in SEQ ID NO: 29.

* * * * *

SEQUENCE LISTING

<160> NUMBER OF SEQ ID NOS: 91

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln

<400> SEQUENCE: 1

Xaa Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120

<210> SEQ ID NO 2
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaggtgcagc tggtggagtc tgggggaggc ttggtaaagc ctggggggtc ccttagactc      60
tcctgtgcag cctctggttt cactttcagt aacgcctgga tgaactgggt ccgccaggct     120
ccagggaagg gactggagtg ggtagccgaa attcgttcta aaagcattaa tagcgccacc     180
cattatgccg aaagcgtgaa aggccggttc accatctcaa gagatgattc aaaaaacacg     240
gtgtatctgc aaatgaacag cctgaaaacc gaggacacag ccgtgtacta ctgcagccgt     300
aattactacg gcagcaccta cgattactgg ggccagggca ccaccctgac cgtgagctcc     360

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala

```
                    20                   25                  30

Trp Met Asn Trp Val Arg Gln Ala Pro Gly Lys Gly Leu Glu Trp Val
            35                  40                  45

Ala Glu Ile Arg Ser Lys Ser Ile Asn Ser Ala Thr His Tyr Ala Glu
 50                  55                  60

Ser Val Lys Gly Arg Phe Thr Ile Ser Arg Asp Asn Ser Lys Lys Thr
 65                  70                  75                  80

Leu Tyr Leu Glu Met Asn Ser Leu Arg Val Glu Asp Thr Ala Val Tyr
                85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser
                115                 120

<210> SEQ ID NO 4
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

caggtgcagc tggtggagtc tgggggaggc ttggtaaagc ctggggggtc ccttagactc     60

tcctgtgcag cctctggttt cactttcagt aacgcctgga tgaactgggt ccgccaggct    120

ccagggaagg gcctggaatg ggtagccgaa attcgttcta aaagcattaa tagcgccacc    180

cattatgccg aaagcgtgaa gggccgattc accatctcca gagacaattc caagaaaacg    240

ttgtatctgg aaatgaacag cctgagagtt gaggacacag ctgtgtacta ctgcagccgt    300

aattactacg gcagcaccta cgattactgg ggccagggca ccaccctgac cgtgagctcc    360

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Leu Thr Gln Ser Pro Asp Phe Gln Ser Val Ser Pro Lys
 1               5                  10                  15

Glu Thr Val Thr Ile Thr Cys Arg Ala Ser Gln Thr Val His Met Ser
                20                  25                  30

Leu His Trp Tyr Gln Gln Lys Pro Asn Gln Ser Pro Arg Leu Leu Ile
            35                  40                  45

Lys Tyr Gly Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Pro
 65                  70                  75                  80

Glu Asp Ala Ala Thr Tyr Tyr Cys Gln Gln Ser His Ser Trp Pro Phe
                85                  90                  95

Thr Phe Gly Ser Gly Thr Asn Val Asp Ile Lys Arg Thr
                100                 105

<210> SEQ ID NO 6
<211> LENGTH: 327
<212> TYPE: DNA
```

<213> ORGANISM: Artificial Sequence
<220> FEATURE:
<223> OTHER INFORMATION: Description of Artificial Sequence: Synthetic
polynucleotide

<400> SEQUENCE: 6
gaaattgtgc tgactcagtc tccagatttt cagtctgtgt ctccaaagga gacagtcacc 60
atcacctgcc gggccagtca gaccgttcat atgagtttac actggtacca gcagaaacca 120
aatcagtctc caaggctcct catcaagtat ggttcccagt ccttctcggg ggtcccctcg 180
aggttcagtg gcagtgggtc tgggacagat ttcaccctca ccatcaatag cctggaacct 240
gaagatgctg caacatacta ctgccagcag agccatagct ggccgttcac cttcggcagc 300
ggcaccaatg tggacatcaa acgtacg 327

<210> SEQ ID NO 7
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

Glu Ile Val Leu Thr Gln Ser Pro Asp Phe Gln Ser Val Ser Pro Lys
1 5 10 15

Glu Thr Val Thr Ile Thr Cys Arg Ala Ser Gln Thr Val His Met Ser
20 25 30

Leu His Trp Tyr Gln Gln Lys Pro Asn Gln Ser Pro Arg Leu Leu Ile
35 40 45

Lys Tyr Gly Ser Gln Ser Phe Ser Gly Val Pro Ser Arg Phe Ser Gly
50 55 60

Ser Gly Ser Gly Thr Asp Phe Thr Leu Thr Ile Asn Ser Leu Glu Pro
65 70 75 80

Glu Asp Ala Ala Thr Tyr Tyr Cys Gln Gln Ser His Phe Trp Pro Phe
85 90 95

Thr Phe Gly Ser Gly Thr Asn Val Asp Ile Lys Arg Thr
100 105

<210> SEQ ID NO 8
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
gaaattgtgc tgactcagtc tccagatttt cagtctgtgt ctccaaagga gacagtcacc 60
atcacctgcc gggccagtca gaccgttcat atgagtttac actggtacca gcagaaacca 120
aatcagtctc caaggctcct catcaagtat ggttcccagt ccttctcggg ggtcccctcg 180
aggttcagtg gcagtgggtc tgggacagat ttcaccctca ccatcaatag cctggaacct 240
gaagatgctg caacatacta ctgccagcag agccatttct ggccgttcac cttcggcagc 300
ggcaccaatg tggacatcaa acgtacg 327

<210> SEQ ID NO 9
<211> LENGTH: 109
<212> TYPE: PRT
<213> ORGANISM: Artificial Sequence -continued
<220> FEATURE:
<223> OTHER INFORMATION: Description of Artificial Sequence: Synthetic
polypeptide

<400> SEQUENCE: 9

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Tyr Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Val Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Asn Val Asp Ile Lys Arg Thr
            100                 105
```

<210> SEQ ID NO 10
<211> LENGTH: 327
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10

```
gaaattgtgc tgactcagtc tccagacttt cagtctgtga ctccaaagga gaaagtcacc     60

atcacctgcc gggccagtca gagcatttat agtagcttac actggtacca gcagaaacca    120

gatcagtctc caaagctcct catcaagttt gcttcccagt ccgtctcagg ggtcccctcg    180

aggttcagtg gcagtggatc tgggacagat ttcaccctca ccatcaatag cctggaagct    240

gaagatgctg caacgtacta ctgccagcag agccatagct ggccgttcac cttcggcagc    300

ggcaccaatg tggacatcaa acgtacg                                        327
```

<210> SEQ ID NO 11
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Tyr Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Val Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Phe Trp Pro Phe
                85                  90                  95
```

```
Thr Phe Gly Ser Gly Thr Asn Val Asp Ile Lys Arg Thr
            100                 105


<210> SEQ ID NO 12
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gaaattgtgc tgactcagtc tccagacttt cagtctgtga ctccaaagga gaaagtcacc     60

atcacctgcc gggccagtca gagcatttat agtagcttac actggtacca gcagaaacca    120

gatcagtctc caaagctcct catcaagttt gcttcccagt ccgtctcagg ggtcccctcg    180

aggttcagtg gcagtggatc tgggacagat ttcaccctca ccatcaatag cctggaagct    240

gaagatgctg caacgtacta ctgccagcag agccatttct ggccgttcac cttcggcagc    300

ggcaccaatg tggacatcaa acgtacg                                        327


<210> SEQ ID NO 13
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Asp Phe Gln Ser Val Ser Pro Lys
1               5                   10                  15

Glu Thr Val Thr Ile Thr Cys Arg Ala Ser Gln Thr Val His Met Ser
            20                  25                  30

Leu His Trp Tyr Gln Gln Lys Pro Asn Gln Ser Pro Arg Leu Leu Ile
        35                  40                  45

Lys Tyr Gly Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Pro
65                  70                  75                  80

Glu Asp Ala Ala Thr Tyr Tyr Cys Gln Gln Ser His Trp Trp Pro Phe
                85                  90                  95

Thr Phe Gly Ser Gly Thr Asn Val Asp Ile Lys Arg Thr
            100                 105


<210> SEQ ID NO 14
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

gaaattgtgc tgactcagtc tccagatttt cagtctgtgt ctccaaagga gacagtcacc     60

atcacctgcc gggccagtca gaccgttcat atgagtttac actggtacca gcagaaacca    120

aatcagtctc caaggctcct catcaagtat ggttcccagt ccttctcggg ggtcccctcg    180

aggttcagtg gcagtgggtc tgggacagat ttcaccctca ccatcaatag cctggaacct    240

gaagatgctg caacatacta ctgccagcag agccattggt ggccgttcac cttcggcagc    300
```

ggcaccaatg tggacatcaa acgtacg 327

<210> SEQ ID NO 15
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Glu Ile Val Leu Thr Gln Ser Pro Asp Phe Gln Ser Val Thr Pro Lys
1 5 10 15

Glu Lys Val Thr Ile Thr Cys Arg Ala Ser Gln Ser Ile Tyr Ser Ser
20 25 30

Leu His Trp Tyr Gln Gln Lys Pro Asp Gln Ser Pro Lys Leu Leu Ile
35 40 45

Lys Phe Ala Ser Gln Ser Val Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys Gln Gln Ser His Trp Trp Pro Phe
85 90 95

Thr Phe Gly Ser Gly Thr Asn Val Asp Ile Lys Arg Thr
100 105

<210> SEQ ID NO 16
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
gaaattgtgc tgactcagtc tccagacttt cagtctgtga ctccaaagga gaaagtcacc 60
atcacctgcc gggccagtca gagcatttat agtagcttac actggtacca gcagaaacca 120
gatcagtctc caaagctcct catcaagttt gcttcccagt ccgtctcagg ggtcccctcg 180
aggttcagtg gcagtggatc tgggacagat ttcaccctca ccatcaatag cctggaagct 240
gaagatgctg caacgtacta ctgtcagcag agccattggt ggccgttcac cttcggcagc 300
ggcaccaatg tggacatcaa acgtacg 327

<210> SEQ ID NO 17
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 18
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gctagcacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480
```

-continued

```
tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

<210> SEQ ID NO 19
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105
```

<210> SEQ ID NO 20
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gtcgctgcac catctgtctt catcttcccg ccatctgatg agcagttgaa atctggaact     60

gcctctgttg tgtgcctgct gaataacttc tatcccagag aggccaaagt acagtggaag    120

gtggataacg ccctccaatc gggtaactcc caggagagtg tcacagagca ggacagcaag    180

gacagcacct acagcctcag cagcaccctg acgctgagca aagcagacta cgagaaacac    240

aaagtctacg cctgcgaagt cacccatcag ggcctgagtt caccggtgac aaagagcttc    300

aacaggggag agtgt                                                     315
```

<210> SEQ ID NO 21
<211> LENGTH: 450
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln

<400> SEQUENCE: 21

```
Xaa Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
```

Glu Ser Asn Gly Gln Pro Glu Asn Asn Tyr Lys Thr Thr Pro Pro Val
385               390                   395                   400

Leu Asp Ser Asp Gly Ser Phe Phe Leu Tyr Ser Lys Leu Thr Val Asp
            405                   410                   415

Lys Ser Arg Trp Gln Gln Gly Asn Val Phe Ser Cys Ser Val Met His
                420                   425                   430

Glu Ala Leu His Asn His Tyr Thr Gln Lys Ser Leu Ser Leu Ser Pro
            435                   440                   445

Gly Lys
    450

<210> SEQ ID NO 22
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| | |
|---|---|
| gaggtgcagc tggtggagtc tgggggaggc ttggtaaagc ctggggggtc ccttagactc | 60 |
| tcctgtgcag cctctggttt cactttcagt aacgcctgga tgaactgggt ccgccaggct | 120 |
| ccagggaagg gactggagtg ggtagccgaa attcgttcta aaagcattaa tagcgccacc | 180 |
| cattatgccg aaagcgtgaa aggccggttc accatctcaa gagatgattc aaaaaacacg | 240 |
| gtgtatctgc aaatgaacag cctgaaaacc gaggacacag ccgtgtacta ctgcagccgt | 300 |
| aattactacg gcagcaccta cgattactgg ggccagggca ccaccctgac cgtgagctcc | 360 |
| gctagcacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 23
<211> LENGTH: 214
<212> TYPE: PRT
<213> ORGANISM: Artificial Sequence -continued
<220> FEATURE:
<223> OTHER INFORMATION: Description of Artificial Sequence: Synthetic
polypeptide

<400> SEQUENCE: 23

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Tyr Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Val Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Trp Trp Pro Phe
                85                  90                  95

Thr Phe Gly Ser Gly Thr Asn Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24

```
gaaattgtgc tgactcagtc tccagacttt cagtctgtga ctccaaagga gaaagtcacc     60

atcacctgcc gggccagtca gagcatttat agtagcttac actggtacca gcagaaacca    120

gatcagtctc caaagctcct catcaagttt gcttcccagt ccgtctcagg ggtcccctcg    180

aggttcagtg gcagtggatc tgggacagat ttcaccctca ccatcaatag cctggaagct    240

gaagatgctg caacgtacta ctgtcagcag agccattggt ggccgttcac cttcggcagc    300

ggcaccaatg tggacatcaa acgtacggtc gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600
```

ctgagttcac cggtgacaaa gagcttcaac aggggagagt gt 642

<210> SEQ ID NO 25
<211> LENGTH: 223
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asn Ser Lys Lys Thr
65                  70                  75                  80

Leu Tyr Leu Glu Met Asn Ser Leu Arg Val Glu Asp Thr Ala Val Tyr
                85                  90                  95

Tyr Cys Ser Arg Asn Tyr Tyr Gly Ser Thr Tyr Gln Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220
```

<210> SEQ ID NO 26
<211> LENGTH: 669
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
caggtgcagc tggtggagtc tgggggaggc ttggtaaagc ctggggggtc ccttagactc     60

tcctgtgcag cctctggttt cactttcagt aacgcctgga tgaactgggt ccgccaggct    120

ccagggaagg gcctggaatg ggtagccgaa attcgttcta aaagcattaa tagcgccacc    180

cattatgccg aaagcgtgaa gggccgattc accatctcca gagacaattc caagaaaacg    240

ttgtatctgg aaatgaacag cctgagagtt gaggacacag ctgtgtacta ctgcagccgt    300

aattactacg gcagcaccta ccagtactgg ggccagggca ccaccctgac cgtgagctcc    360

gctagcacca agggcccatc ggtcttcccc ctggcaccct cctccaagag cacctctggg    420
```

```
ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgt                                                            669
```

```
<210> SEQ ID NO 27
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Gln Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220
```

```
<210> SEQ ID NO 28
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

gaggtgcagc tggtggagtc tgggggaggc ttggtaaagc ctggggggtc ccttagactc     60

tcctgtgcag cctctggttt cactttcagt aacgcctgga tgaactgggt ccgccaggct    120
```

-continued

```
ccagggaagg gactggagtg ggtagccgaa attcgttcta aaagcattaa tagcgccacc    180

cattatgccg aaagcgtgaa aggccggttc accatctcaa gagatgattc aaaaaacacg    240

gtgtatctgc aaatgaacag cctgaaaacc gaggacacag ccgtgtacta ctgcagccgt    300

aattactacg gcagcaccta ccagtactgg ggccagggca ccaccctgac cgtgagctcc    360

gctagcacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgt                                                            669
```

```
<210> SEQ ID NO 29
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Leu Thr Gln Ser Pro Asp Phe Gln Ser Val Ser Pro Lys
1               5                   10                  15

Glu Thr Val Thr Ile Thr Cys Arg Ala Ser Gln Thr Val His Met Ser
            20                  25                  30

Leu His Trp Tyr Gln Gln Lys Pro Asn Gln Ser Pro Arg Leu Leu Ile
        35                  40                  45

Lys Tyr Gly Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Pro
65                  70                  75                  80

Glu Asp Ala Ala Thr Tyr Tyr Cys Gln Gln Ser His Lys Trp Pro Phe
                85                  90                  95

Thr Phe Gly Ser Gly Thr Asn Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 30
<211> LENGTH: 642
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 30

```
gaaattgtgc tgactcagtc tccagatttt cagtctgtgt ctccaaagga gacagtcacc     60

atcacctgcc gggccagtca gaccgttcat atgagtttac actggtacca gcagaaacca    120

aatcagtctc caaggctcct catcaagtat ggttcccagt ccttctcggg ggtcccctcg    180

aggttcagtg gcagtgggtc tgggacagat ttcaccctca ccatcaatag cctggaacct    240

gaagatgctg caacatacta ctgccagcag agccataaat ggccgttcac cttcggcagc    300

ggcaccaatg tggacatcaa acgtacggtc gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagttcac cggtgacaaa gagcttcaac aggggagagt gt                       642
```

<210> SEQ ID NO 31
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Tyr Ser Ser
            20                  25                  30

Leu His Trp Tyr Gln Gln Lys Pro Asp Gln Ser Pro Lys Leu Leu Ile
        35                  40                  45

Lys Phe Ala Ser Gln Ser Val Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Lys Trp Pro Phe
                85                  90                  95

Thr Phe Gly Ser Gly Thr Asn Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 32
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
gaaattgtgc tgactcagtc tccagacttt cagtctgtga ctccaaagga gaaagtcacc 60
atcacctgcc gggccagtca gagcatttat agtagcttac actggtacca gcagaaacca 120
gatcagtctc caaagctcct catcaagttt gcttcccagt ccgtctcagg ggtcccctcg 180
aggttcagtg gcagtggatc tgggacagat ttcaccctca ccatcaatag cctggaagct 240
gaagatgctg caacgtacta ctgccagcag agccataaat ggccgttcac cttcggcagc 300
ggcaccaatg tggacatcaa acgtacggtc gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagttcac cggtgacaaa gagcttcaac aggggagagt gt 642

<210> SEQ ID NO 33
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val

<210> SEQ ID NO 34
<211> LENGTH: 294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
gctagcacca agggcccatc ggtcttcccc ctggcaccct cctccaagag cacctctggg 60
ggcacagcgg ccctgggctg cctggtcaag gactacttcc ccgaaccggt gacggtgtcg 120

```
tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agtt          294


<210> SEQ ID NO 35
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

gtcgactaat acgactcact ataggggaat tgtgagcgga taacaattcc cctctagaaa     60

taattttgtt taactttaag aaggaggcgg ccgc                                 94


<210> SEQ ID NO 36
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Gly Ser Ser Ser
65                  70                  75                  80

Arg Thr Pro Ser Asp Lys Pro Val Ala His Val Val Ala Asn Pro Gln
                85                  90                  95

Ala Glu Gly Gln Leu Gln Trp Leu Asn Arg Arg Ala Asn Ala Leu Leu
            100                 105                 110

Ala Asn Gly Val Glu Leu Arg Asp Asn Gln Leu Val Val Pro Ser Glu
        115                 120                 125

Gly Leu Tyr Leu Ile Tyr Ser Gln Val Leu Phe Lys Gly Gln Gly Cys
    130                 135                 140

Pro Ser Thr His Val Leu Leu Thr His Thr Ile Ser Arg Ile Ala Val
145                 150                 155                 160

Ser Tyr Gln Thr Lys Val Asn Leu Leu Ser Ala Ile Lys Ser Pro Cys
                165                 170                 175

Gln Arg Glu Thr Pro Glu Gly Ala Glu Ala Lys Pro Trp Tyr Glu Pro
            180                 185                 190

Ile Tyr Leu Gly Gly Val Phe Gln Leu Glu Lys Gly Asp Arg Leu Ser
        195                 200                 205

Ala Glu Ile Asn Arg Pro Asp Tyr Leu Asp Phe Ala Glu Ser Gly Gln
    210                 215                 220

Val Tyr Phe Gly Ile Ile Ala Leu
225                 230
```

<210> SEQ ID NO 37
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
atgagcactg aaagcatgat ccgggacgtg gagctggccg aggaggcgct ccccaagaag     60

acagggggc cccagggctc caggcggtgc ttgttcctca gcctcttctc cttcctgatc    120

gtggcaggcg ccaccacgct cttctgcctg ctgcactttg gagtgatcgg cccccagagg    180

gaagagttcc ccagggacct ctctctaatc agccctctgg cccaggcagg atcatcttct    240

cgaaccccga gtgacaagcc tgtagcccat gttgtagcaa accctcaagc tgaggggcag    300

ctccagtggc tgaaccgccg ggccaatgcc ctcctggcca atggcgtgga gctgagagat    360

aaccagctgg tggtgccatc agagggcctg tacctcatct actcccaggt cctcttcaag    420

ggccaaggct gcccctccac ccatgtgctc ctcacccaca ccatcagccg catcgccgtc    480

tcctaccaga ccaaggtcaa cctcctctct gccatcaaga gcccctgcca gagggagacc    540

ccagaggggg ctgaggccaa gccctggtat gagcccatct atctgggagg ggtcttccag    600

ctggagaagg gtgaccgact cagcgctgag atcaatcggc ccgactatct cgactttgcc    660

gagtctggac aggtctactt tgggatcatt gccctg                             696
```

<210> SEQ ID NO 38
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Met Ser Thr Glu Ser Met Ile Arg Asp Val Glu Leu Ala Glu Glu Ala
1               5                   10                  15

Leu Pro Arg Lys Thr Ala Gly Pro Gln Gly Ser Arg Arg Cys Trp Phe
            20                  25                  30

Leu Ser Leu Phe Ser Phe Leu Leu Val Ala Gly Ala Thr Thr Leu Phe
        35                  40                  45

Cys Leu Leu His Phe Gly Val Ile Gly Pro Gln Arg Glu Glu Phe Pro
    50                  55                  60

Lys Asp Pro Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Thr Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Asn His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
```

```
            180                 185                 190

Pro Ile Tyr Leu Gly Gly Val Phe Gln Leu Glu Lys Gly Asp Arg Leu
        195                 200                 205

Ser Ala Glu Ile Asn Leu Pro Asp Tyr Leu Asp Phe Ala Glu Ser Gly
    210                 215                 220

Gln Val Tyr Phe Gly Ile Ile Ala Leu
225                 230
```

<210> SEQ ID NO 39
<211> LENGTH: 699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
atgagcactg aaagcatgat ccgggacgtg gagctggccg aggaggcgct cccaaggaag     60

acagcggggc cccagggctc caggcggtgc tggttcctca gcctcttctc cttcctgctc    120

gtggcaggcg ccaccacgct cttctgtctg ctgcactttg gagtgatcgg cccccagagg    180

gaagagttcc ccaaggaccc ctctctaatc agccctctgg ctcaggcagt cagatcatct    240

tctcgaaccc caagtgacaa gcctgtagcc catgttgtag caaaccctca agctgagggg    300

cagctccagt ggctgaaccg ccgggccaat gccctcctgg ccaatggcgt ggagctgaca    360

gataaccagc tggtggtgcc atcagaaggc ctgtacctca tctactccca ggtcctcttc    420

aagggccaag gctgcccctc caaccatgtg ctcctcaccc acaccatcag ccgcatcgcc    480

gtctcctacc agaccaaggt caacctcctc tctgccatca agagcccctg ccagagggag    540

actccagagg gggctgaggc caagccctgg tatgagccca tctacctagg aggggtcttt    600

cagctggaga agggtgatcg actcagcgct gagatcaatc tgcccgacta tctcgacttt    660

gccgagtctg ggcaggtcta ctttgggatc attgccctg                           699
```

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 40

```
gcgaattcag gtsmarctgc agsagtcwgg                                      30
```

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 41

```
tgaggagacg gtgaccgtgg tcccttggcc ccag                                 34
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gacattctgm tsacmcagmc tcc 23

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gttagatctc gagcttggtc cc 22

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
cggaattccg tacgtttcac ttccagattg g 31

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
ccgctcgagg cgctcacggt cagggtggtg ccctg 35

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (16)..(16)
<223> OTHER INFORMATION: a, c, t, g, unknown or other

<400> SEQUENCE: 46
gcaacctact actgcnbkca gagccatagc tgg 33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
gcaacctact actgcdakca gagccatagc tgg 33

<210> SEQ ID NO 48
<211> LENGTH: 33
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 48
gcaacctact actgccatca gagccatagc tgg 33

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (19)..(19)
<223> OTHER INFORMATION: a, c, t, g, unknown or other

<400> SEQUENCE: 49
gcaacctact actgccagnb kagccatagc tggccg 36

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
gcaacctact actgccagda kagccatagc tggccg 36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
gcaacctact actgccagca tagccatagc tggccg 36

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
gcaacctact actgccagca gbdkcatagc tggccgttc 39

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
gcaacctact actgccagca gvctcatagc tggccgttc 39

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
gcaacctact actgccagca gawkcatagc tggccgttc 39

<210> SEQ ID NO 55
<211> LENGTH: 42
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (25)..(25)
<223> OTHER INFORMATION: a, c, t, g, unknown or other

<400> SEQUENCE: 55
gcaacctact actgccagca gagcnbkagc tggccgttca cc 42

<210> SEQ ID NO 56
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
gcaacctact actgccagca gagcdakagc tggccgttca cc 42

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
gcaacctact actgccagca gagccagagc tggccgttca cc 42

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
gcaacctact actgccagca gagccatbdk tggccgttca ccttc 45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
gcaacctact actgccagca gagccatvct tggccgttca ccttc 45

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gcaacctact actgccagca gagccatawk tggccgttca ccttc 45

<210> SEQ ID NO 61
<211> LENGTH: 48
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (32)..(32)
<223> OTHER INFORMATION: a, c, t, g, unknown or other

<400> SEQUENCE: 61
gcaacctact actgccagca gagccatagc hnkccgttca ccttcggc 48

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (31)..(31)
<223> OTHER INFORMATION: a, c, t, g, unknown or other

<400> SEQUENCE: 62
gcaacctact actgccagca gagccatagc ngtccgttca ccttcggc 48

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (34)..(34)
<223> OTHER INFORMATION: a, c, t, g, unknown or other

<400> SEQUENCE: 63
gcaacctact actgccagca gagccatagc tggndkttca ccttcggcag c 51

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gcaacctact actgccagca gagccatagc tggdctttca ccttcggcag c 51

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (17)..(17)
<223> OTHER INFORMATION: a, c, t, g, unknown or other

<400> SEQUENCE: 65
gtattactgc agccgtnbkt actacggcag cacc 34

<210> SEQ ID NO 66
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
gtattactgc agccgtbakt actacggcag cacc 34

<210> SEQ ID NO 67
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
gtattactgc agccgtaaat actacggcag cacc 34

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (20)..(20)
<223> OTHER INFORMATION: a, c, t, g, unknown or other

<400> SEQUENCE: 68
gtattactgc agccgtaatn bktacggcag cacctacg 38

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gtattactgc agccgtaatv aktacggcag cacctacg 38

<210> SEQ ID NO 70
<211> LENGTH: 43
<212> TYPE: DNA
<213> ORGANISM: Artificial Sequence
<220> FEATURE:

<223> OTHER INFORMATION: Description of Artificial Sequence: Synthetic
primer
<220> FEATURE:
<221> NAME/KEY: modified_base
<222> LOCATION: (23)..(23)
<223> OTHER INFORMATION: a, c, t, g, unknown or other

<400> SEQUENCE: 70
gtattactgc agccgtaatt acnbkggcag cacctacgat tac 43

<210> SEQ ID NO 71
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
gtattactgc agccgtaatt acvakggcag cacctacgat tac 43

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (26)..(26)
<223> OTHER INFORMATION: a, c, t, g, unknown or other

<400> SEQUENCE: 72
gtattactgc agccgtaatt actacnhkag cacctacgat tactg 45

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
gtattactgc agccgtaatt actachgkag cacctacgat tactg 45

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
gtattactgc agccgtaatt actacggcbd kacctacgat tactgggc 48

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
gtattactgc agccgtaatt actacggcvc tacctacgat tactgggc 48

<210> SEQ ID NO 76
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
gtattactgc agccgtaatt actacggcaw kacctacgat tactgggc 48

<210> SEQ ID NO 77
<211> LENGTH: 50
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (32)..(32)
<223> OTHER INFORMATION: a, c, t, g, unknown or other

<400> SEQUENCE: 77
gtattactgc agccgtaatt actacggcag cndktacgat tactgggccc 50

<210> SEQ ID NO 78
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
gtattactgc agccgtaatt actacggcag cbcttacgat tactgggccc 50

<210> SEQ ID NO 79
<211> LENGTH: 53
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (35)..(35)
<223> OTHER INFORMATION: a, c, t, g, unknown or other

<400> SEQUENCE: 79
gtattactgc agccgtaatt actacggcag caccnbkgat tactggggcc agg 53

<210> SEQ ID NO 80
<211> LENGTH: 53
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gtattactgc agccgtaatt actacggcag caccvakgat tactggggcc agg 53

<210> SEQ ID NO 81
<211> LENGTH: 55
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (38)..(38)
<223> OTHER INFORMATION: a, c, t, g, unknown or other

<400> SEQUENCE: 81
gtattactgc agccgtaatt actacggcag cacctacnbk tactggggcc agggc 55

<210> SEQ ID NO 82
<211> LENGTH: 55
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
gtattactgc agccgtaatt actacggcag cacctachak tactggggcc agggc 55

<210> SEQ ID NO 83
<211> LENGTH: 55
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
gtattactgc agccgtaatt actacggcag cacctacgaa tactggggcc agggc 55

<210> SEQ ID NO 84
<211> LENGTH: 58
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (41)..(41)
<223> OTHER INFORMATION: a, c, t, g, unknown or other

<400> SEQUENCE: 84
gtattactgc agccgtaatt actacggcag cacctacgat nbktggggcc agggcacc 58

<210> SEQ ID NO 85
<211> LENGTH: 58
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
gtattactgc agccgtaatt actacggcag cacctacgat vaktggggcc agggcacc 58

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86

-continued

```
tgaaagctta tggaaattgt gctgactcag tctc                            34


<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

aatctcgagt caacactctc ccctgttgaa gct                             33


<210> SEQ ID NO 88
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

actggtacca tggaggtgca gctggtggag tctgggg                         37


<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

gatgggccct tggtgctagc ggagctcacg gtcagggtgg tgccc                45


<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

gatgggccct tggtgctagc ggagctcacg gtcagggtgg tgccc                45


<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

aatctcgagt catttacccg gagacaggga gagg                            34
```